United States Patent
Horvath et al.

(10) Patent No.: US 6,362,186 B1
(45) Date of Patent: Mar. 26, 2002

(54) AMINOALKYL SUBSTITUTED 9H-PHRIDINO[2,3-B] INDOLE AND 9H-PYRIMIDINO[4,5-B] INDOLE DERIVATIVES

(75) Inventors: Raymond F. Horvath, North Branford; James W. Darrow, Wallingford; George D. Maynard, Clinton, all of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/707,387

(22) Filed: Nov. 6, 2000

Related U.S. Application Data

(63) Continuation of application No. 09/283,409, filed on Apr. 1, 1999, now Pat. No. 6,147,085.
(60) Provisional application No. 60/080,451, filed on Apr. 2, 1998.

(51) Int. Cl.[7] ............ C07D 239/70; C07D 487/04; A61K 31/542; A61P 9/12; A61P 25/22
(52) U.S. Cl. ............... 514/252.1; 514/267; 544/250; 544/106; 544/336; 544/361; 540/476; 540/597; 546/87
(58) Field of Search .............. 544/250; 514/267, 514/252.1

(56) References Cited

FOREIGN PATENT DOCUMENTS

WO      98/29397    *   9/1998

\* cited by examiner

Primary Examiner—Richard L. Raymond
Assistant Examiner—Venkataraman Balasubramanian
(74) Attorney, Agent, or Firm—McDonnell Boehnen Hulbert & Berghoff

(57) ABSTRACT

Disclosed are compounds of the formula:

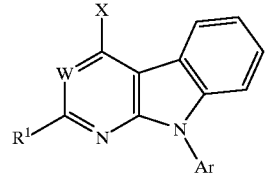

wherein Ar, $R^1$, W and X are substituents as defined herein, which compounds are (1) antagonists at $CRF_1$ receptors and are, therefore, useful in the diagnosis and treatment of stress related disorders such as post traumatic stress disorder (PTSD) as well as depression, headache and anxiety; and (2) are neuropeptide $Y_1$, receptor antagonists, and are therefore useful in the treatment of a variety of clinical conditions which are characterized by the presence of an excess of neuropeptide Y.

31 Claims, No Drawings

AMINOALKYL SUBSTITUTED 9H-PHRIDINO[2,3-B] INDOLE AND 9H-PYRIMIDINO[4,5-B] INDOLE DERIVATIVES

This is a continuation of application Ser. No. 09/283,409, filed Apr. 1, 1999 now U.S. Pat. No. 6,147,085, which is a continuation of application Ser. No. 60/080,451, filed Apr. 2, 1998.

BACKGROUND OF THE INVENTION

1. Field of the Invention

The present invention relates to aminoalkyl substituted 9H-pyridino[2,3-b]indole and 9H-pyrimidino[4,5-b]indole derivatives which selectively bind to corticotropin-releasing factor ($CRF_1$) receptors and to mammalian neuropeptide Y ($NPY_1$) receptors. It further relates to pharmaceutical compositions containing such compounds and the use of such compounds in treating physiological disorders induced or facilitated by CRF or those associated with an excess of neuropeptide Y.

2. Description of the Related Art

Corticotropin releasing factor (herein referred to as CRF), a 41 amino acid peptide, is the primary physiological regulator of proopiomelanocortin (POMC) derived peptide secretion from the anterior pituitary gland [J. Rivier et al., *Proc. Nat. Acad. Sci.* (*USA*) 80:4851 (1983); W. Vale et al., *Science* 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989). Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147(1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines [C. W Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro 15-1788), which was without behavioral activity alone in the operant conflict test, reversed the effects of CRF in a dose-dependent manner while the benzodiazepine inverse agonist (FG 7142) enhanced the actions of CRF [K. T. Britton et al., *Psychopharmacology* 94:306 (1988)].

It has been further postulated that CRF has a role in immunological, cardiovascular or heart-related diseases such as hypertension, tachycardia and congestive heart failure, stroke and osteoporosis. CRF has also been implicated in premature birth, psychosocial dwarfism, stress-induced fever, ulcer, diarrhea, post-operative ileus and colonic hypersensitivity associated with psychopathological disturbance and stress.

The mechanisms and sites of action through which the standard anxiolytics and antidepressants produce their therapeutic effects remain to be elucidated. It has been hypothesized however, that they are involved in the suppression of the CRF hypersecretion that is observed in these disorders. of particular interest is that preliminary studies examining the effects of a CRF receptor antagonist (α-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C .B Nemeroff eds., CRC Press p221 (1990)].

Neuropeptide Y, a peptide first isolated in 1982, is widely distributed in the central and peripheral neurons and is responsible for a multitude of biological effects in the brain and the periphery. Various animal studies have shown that activation of neuropeptide $NPY_1$ receptors is related to vasoconstriction, Wahlestedt et al., *Regul. Peptides*, 13: 307–318 (1986), McCauley and Westfall, *J. Pharmacol. Exp. Ther.* 261 863–868 (1992), and Grundemar et al., *Br. J. Pharmacol.* 105: 45–50 (1992); and to stimulation of consummatory behavior, Flood and Morley, *Peptides*, 10: 963–966 (1989), Leibowitz and Alexander, *Peptides*, 12: 1251–1260 (1991), and Stanley et al., *Peptides*, 13: 581–587

(1992). Grundemar and Hakanson, *TiPS*, 15: 153–159 (1994), state that, in animals, neuropeptide Y is a powerful stimuli of food intake, and an inducer of vasoconstriction leading to hypertension. They further point out that low levels of neuropeptide Y is associated with loss of appetite. These reports clearly indicate that compounds that inhibit the activity of this protein will reduce hypertension and appetite in animals.

SUMMARY OF THE INVENTION

This invention provides novel compounds of Formula I which interact with $CRF_1$ receptors and $NPY_1$ receptors. It further relates to the use of such compounds, pharmaceutical compositions comprising these compounds, and methods useful for the treatment of psychiatric and affective disorders and neurological diseases, including major depression, headaches, anxiety-related disorders, post-traumatic stress disorder, supranuclear palsy, as well as treatment of immunological, cardiovascular or heart-related diseases, hypertension, feeding disorders, diabetes, dislipidemia, colonic hypersensitivity associated with psychopathological disturbance, and stress. It further relates to the use of such compounds in treating physiological disorders induced or facilitated by CRF or those associated with an excess of neuropeptide Y. In particular, this invention provides aminoalkyl substituted 9H-pyridino[2,3-b]indole and 9H-pyrimidino[4,5-b]indole derivatives of Formula I which selectively bind to corticotropin-releasing factor ($CRF_1$) receptors and/or to mammalian neuropeptide Y ($NPY_1$) receptors.

Accordingly, a broad embodiment of the invention is directed to a compound of Formula I:

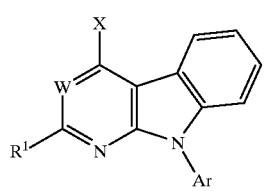

wherein

Ar is phenyl, 1- or 2-naphthyl, 2-, 3-, or 4-pyridyl, 2-, 4- or 5-pyrimidinyl, optionally mono-, di-, or tri-substituted with halogen, trifluoromethyl, hydroxy, amino, lower alkylamino, lower dialkylamino, carboxamido, N-lower alkyl carboxamido, N,N-lower dialkyl carboxamido, $C_1$–$C_6$ alkyl, $C_1$–$C_6$ alkoxy, with the proviso that at least one of the positions ortho or para to the point of attachment of Ar to the tricyclic ring system is substituted;

$R^1$ is hydrogen, halogen, trifluoromethyl, $C_1$–$C_6$ alkyl, or ($C_1$–$C_6$ alkyl)-$G^1$—$R^2$ where $G^1$ is oxygen or sulfur and $R^1$ is hydrogen or $C_1$–$C_6$ alkyl;

W is N or C—$R^3$ where $R^3$ is hydrogen or $C_1$–$C_6$ alkyl; and

X is

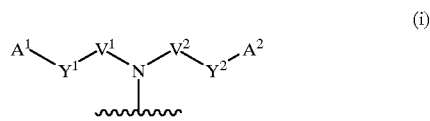

wherein $V^1$ and $V^2$ are $CH_2$, CO, CS, $SO_2$ or $CH(C_1$–$C_6$ alkyl), with the proviso that both $V^1$ and $V^2$ cannot both be CO, CS or $SO_2$;

$Y^1$ and $Y^2$ independently represent a bond or $C_1$–$C_6$ alkylene;

$A^1$ is $NR^4R^5$ wherein $R^4$ and $R^5$ are independently hydrogen, a lower alkyl group which optionally forms a heterocycloalkyl group with $Y^1$;

$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

lower alkanoyl, lower alkylsulfonyl, with the proviso that $R^4$ and $R^5$ cannot both be alkanoyl or alkylsulfonyl; or $NR^4R^5$ taken together form a $C_3$–$C_6$ heterocycloalkyl or a group of the formula:

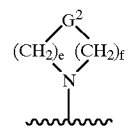

wherein e and f are independently 1, 2 or 3 and the sum of e and f is at least 3; and $G^2$ is $NR^6$ wherein $R^6$ is hydrogen or $C_1$–$C_6$ alkyl, or $CH(C_0$–$C_6$ alkylene)-$G^3$—$R^7$ wherein $G^3$ is CONH, CONH($C_1$–$C_6$ alkyl), NH, NH($C_1$–$C_6$ alkyl) and $R^7$ is hydrogen or $C_1$–$C_6$ alkyl; or $CONH_2$, $CO[N(C_1$–$C_6$ alkyl)$R^8$] wherein $R^8$ is hydrogen or $C_1$–$C_6$ alkyl;

$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

A is hydrogen, $C_1$–$C_6$ alkyl, ($C_1$–$C_6$ alkylene)-$G^4$—$R^9$ wherein $G^4$ is oxygen or sulfur and $R^9$ is hydrogen, trifluoromethyl or $C_1$–$C_6$ alkyl;

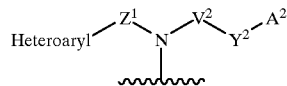

(ii)

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or disubstituted with halogen, trifluoromethyl, amino, $C_1$–$C_6$ alkyl, $C_1$–$C_6$ alkoxy, with the proviso that tetrazolyl can have at most one substituent;

$Z^1$ is $C_1$–$C_6$ alkyl; and $V^2$, $Y^2$ and $A^2$ are as defined above;

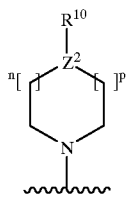

(iii)

where
$Z^2$ is carbon or nitrogen;
where
when $Z^2$ is CH, n is 0, 1, 2 or 3 and p is 1, 2, or 3, $R^{10}$ is carboxamido, or ($C_0$–$C_6$ alkylene)-$G^5$—$R^{11}$ wherein $G^5$ is NH, NH($C_1$–$C_6$ alkyl) and $R^{11}$ is hydrogen, $C_1$–$C_6$ alkyl, $C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;
when $Z^2$ is carbon, n is 1 or 2 and p is 1 or 2, $R^{10}$ is amino; or
when $Z^2$ is nitrogen, n is 1 or 2 and p is 1 or 2, $R^{10}$ is hydrogen; or (iv) a nitrogen heterocycle of the formula:

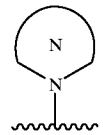

wherein the N-ring represents triazolyl, tetrazolyl, imidazolyl, or pyrazolyl, each of which is optionally substituted with amino, trifluoromethyl, carboxamido, or ($C_1$–$C_6$ alkylene)-$G^6$—$R^{12}$ wherein $G^6$ is NH, NH($C_1$–$C_6$ alkyl) and $R^{12}$ is hydrogen, $C_1$–$C_6$ alkyl, $C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring.

The compounds of Formula I are antagonists at the $CRF_1$ receptor and are useful in the diagnosis and treatment of stress related disorders such as post traumatic stress disorder (PTSD) as well as depression, headache and anxiety.

They are useful in methods for the treatment of psychiatric and affective disorders and neurological diseases, including major depression, headaches, anxiety-related disorders, post-traumatic stress disorder, supranuclear palsy, as well as treatment of immunological, cardiovascular or heart-related diseases, hypertension, feeding disorders, diabetes, dislipidemia, colonic hypersensitivity associated with psychopathological disturbance, and stress. Such methods involve administration to a mammal of an effective amount of a compound of the invention.

The compounds of Formula I are also neuropeptide $Y_1$ receptor antagonists, and, therefore, are also of value in the treatment of a wide variety of clinical conditions which are characterized by the presence of an excess of neuropeptide Y. The compounds of Formula I have different chemical structures which affect their selectivity towards either the $CRF_1$ or the $NPY_1$ receptors.

DETAILED DESCRIPTION OF THE INVENTION

The novel compounds encompassed by the instant invention can be described by general Formula I:

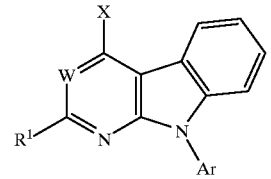

I wherein

Ar is phenyl, 1- or 2-naphthyl, 2-, 3-, or 4-pyridyl, 2-, 4- or 5-pyrimidinyl, optionally mono-, di-, or tri-substituted with halogen, trifluoromethyl, hydroxy, amino, lower alkylamino, lower dialkylamino, carboxamidb, N-lower alkyl carboxamido, N,N-lower dialkyl carboxamido, $C_1$–$C_6$ alkyl, $C_1$–$C_6$ alkoxy, with the proviso that at least one of the positions ortho or para to the point of attachment of Ar to the tricyclic ring system is substituted;

$R^1$ is hydrogen, halogen, trifluoromethyl, $C_1$–$C_6$ alkyl, or ($C_1$–$C_6$ alkyl)-$G^1$—$R^2$ where $G^1$ is oxygen or sulfur and $R^2$ is hydrogen or $C_1$–$C_6$ alkyl;

W is N or C—$R^3$ where $R^3$ is hydrogen or $C_1$–$C_6$ alkyl; and

X is

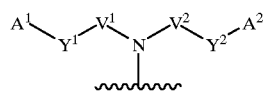
(i)

wherein
$V^1$ and $V^2$ are $CH_2$, CO, CS, $SO_2$ or $CH(C_1-C_6$ alkyl), with the proviso that both $V^1$ and $V^2$ cannot both be CO, CS or $SO_2$;
$Y^1$ and $Y^2$ independently represent a bond or $C_1-C_6$ alkylene;
$A^1$ is $NR^4R^5$ wherein $R^4$ and $R^5$ are independently hydrogen, a lower alkyl group which optionally forms a heterocycloalkyl group with $Y^1$;
$C_1-C_6$ arylalkyl or $C_1-C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;
lower alkanoyl, lower alkylsulfonyl, with the proviso that $R^4$ and $R^5$ cannot both be alkanoyl or alkylsulfonyl; or
$NR^4R^5$ taken together form a $C_3-C_6$ heterocycloalkyl or a group of the formula:

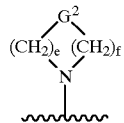

wherein e and f are independently 1, 2 or 3 and the sum of e and f is at least 3; and
$G^2$ is
$NR^6$ wherein $R^6$ is hydrogen or $C_1-C_6$ alkyl, or $CH(C_0-C_6$ alkylene)-$G^3$—$R^7$ wherein $G^3$ is CONH, CONH($C_1-C_6$ alkyl), NH, NH($C_1-C_6$ alkyl) and $R^7$ is hydrogen or $C_1-C_6$ alkyl; or $CONH_2$, $CO[N(C_1-C_6$ alkyl)$R^8$] wherein $R^8$ is hydrogen or $C_1-C_6$ alkyl;
$C_1-C_6$ arylalkyl or $C_1-C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

$A^2$ is hydrogen, $C_1-C_6$ alkyl, ($C_1-C_6$ alkylene)-$G^4$—$R^9$ wherein $G^4$ is oxygen or sulfur and $R^9$ is hydrogen, trifluoromethyl or $C_1-C_6$ alkyl;

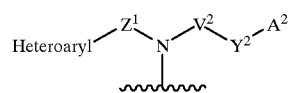
(ii)

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or disubstituted with halogen, trifluoromethyl, amino, $C_1-C_6$ alkyl, $C_1-C_6$ alkoxy, with the proviso that tetrazolyl can have at most one substituent;
$Z^1$ is $C_1-C_6$ alkyl; and
$V^2$, $Y^2$ and $A^2$ are as defined above;

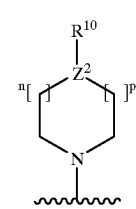
(iii)

where
$Z^2$ is carbon or nitrogen;
where
when $Z^2$ is CH, n is 0, 1, 2 or 3 and p is 1, 2, or 3, $R^{10}$ is carboxamido, or ($C_0-C_6$ alkylene)-$G^5$—$R^{11}$ wherein $G^5$ is NH, NH($C_1-C_6$ alkyl) and $R^{11}$ is hydrogen, $C_1-C_6$ alkyl, $C_1-C_6$ arylalkyl or $C_1-C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;
when $Z^2$ is carbon, n is 1 or 2 and p is 1 or 2, $R^{10}$ is amino; or
when $Z^2$ is nitrogen, n is 1 or 2 and p is 1 or 2, $R^{10}$ is hydrogen; or
(iv) a nitrogen heterocycle of the formula:

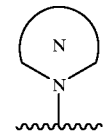

wherein the N-ring represents triazolyl, tetrazolyl, imidazolyl, or pyrazolyl, each of which is optionally substituted with amino, trifluoromethyl, carboxamido, or $(C_1-C_6$ alkylene$)-G^6-R^{12}$ wherein $G^6$ is NH, NH$(C_1-C_6$ alkyl) and $R^{12}$ is hydrogen, $C_1-C_6$ alkyl, $C_1-C_6$ arylalkyl or $C_1-C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring.

Preferred compounds of Formula I include those of Formula IA:

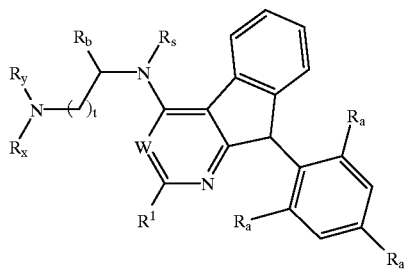

IA wherein each $R_a$ is $C_1-C_6$ alkyl;

$R_b$ is hydrogen or methyl;

$R_1$ is $C_1-C_6$ alkyl;

$R_s$ is $C_1-C_6$ alkyl, $(C_3-C_5)$cycloalkyl$(C_1-C_3)$alkyl, $(C_1-C_3)$alkoxy$(C_1-C_3)$alkyl, or $(C_3-C_5)$cycloalkyl;

t is 1, 2 or 3; and $R_x$ is hydrogen, $C_1-C_6$ alkyl, phenyl$(C_1-C_6)$alkyl where phenyl is optionally mono- or disubstituted independently with $C_1-C_6$ alkyl, $C_1-C_6$ alkoxy, halogen, or hydroxy; and $R_y$ is hydrogen, $C_1-C_6$ alkyl, $(C_3-C_6)$cycloalkyl; or $NR_xR_y$ represents pyrrolidinyl, N-$(C_1-C_6)$ alkylpyrrolidin-2-yl, piperidinyl, morpholinyl, or N-$(C_1-C_6)$alkylpiperazinyl.

Preferred compounds of Formula IA include those where $R_s$ is $C_1-C_6$ alkyl or cyclopropylmethyl. Other preferred compounds of Formula IA include those where $R_s$ is cyclopropyl$(C_1-C_3)$alkyl. Still other preferred compounds of Formula IA include those where $R_x$ and $R_y$ independently represent hydrogen or $C_1-C_2$ alkyl. More preferred compounds of IA include those where $R_s$ is cyclopropyl$(C_1-C_3)$ alkyl, $R_x$ and $R_y$ independently represent hydrogen or $C_1-C_2$ alkyl; and each $R_a$ is methyl. Particularly preferred compounds of IA are those W is nitrogen.

Other preferred compounds of Formula I include those of Formula IB:

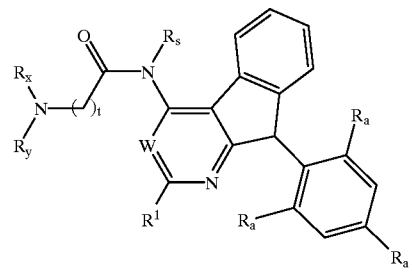

IB wherein
each $R_a$ is $C_1-C_6$ alkyl;
$R_1$ is $C_1-C_6$ alkyl;
$R_s$ is $C_1-C_6$ alkyl, cyclopropyl$(C_1-C_3)$alkyl or $(C_1-C_3)$ alkoxy$(C_1-C_3)$alkyl;
t is 1 or 2;
$R_x$ is hydrogen, $C_1-C_6$ alkyl, phenyl$(C_1-C_6)$alkyl where phenyl is optionally mono- or disubstituted independently with $C_1-C_6$ alkyl, $C_1-C_6$ alkoxy, halogen, or hydroxy; and
$R_y$ is hydrogen, $C_1-C_6$ alkyl, $(C_3-C_6)$cycloalkyl; or
$NR_xR_y$ represents pyrrolidinyl, N-$(C_1-C_6)$ alkylpyrrolidin-2-yl, piperidinyl, morpholinyl, or N-$(C_1-C_6)$alkylpiperazinyl.

Preferred compounds of Formula IB include those where $R_s$ is $C_1-C_6$ alkyl or cyclopropylmethyl. Other preferred compounds of Formula IB include those where $R_s$ is cyclopropyl$(C_1-C_3)$alkyl. Yet other preferred compounds of Formula IB include those where t is 1 and $R_x$ and $R_y$ independently represent hydrogen or $C_1-C_2$ alkyl. More preferred compounds of Formula IB include those where $R_s$ is cyclopropyl$(C_1-C_3)$alkyl, t is 1 and $R_x$ and $R_y$ independently represent hydrogen or $C_1-C_2$ alkyl. Particularly preferred compounds of IB are those where each $R_a$ is methyl, $R_s$ is cyclopropyl$(C_1-C_3)$alkyl, t is 1 and $R_x$ and $R_y$ independently represent hydrogen or $C_1-C_2$ alkyl. Highly preferred compounds of Formula IB are those where W is nitrogen.

Other preferred compounds of Formula I include those of Formula IC:

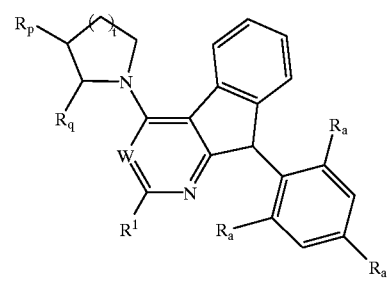

IC wherein
each $R_a$ is $C_1-C_6$ alkyl;
$R_1$ is $C_1-C_6$ alkyl;
t is 1 or 2;
$R_x$ and $R_y$ are different and represent hydrogen; $(C_3-C_7)$ cycloalkylamino $(C_1-C_3)$alkyl, carboxamido, $(C_3-C_7)$ cycloalkylamino, $C_2-C_6$ alkanoyl optionally substituted in the ω-position with $C_1-C_6$ alkyl or phenyl optionally mono- or disubstituted independently with $C_1$–$C_6$ alkyl, $C_1$–$C_6$ alkoxy, halogen, or hydroxy, provided that at least one of $R_x$ and $R_y$ is hydrogen.

Preferred compounds of Formula IC include those wherein $R^1$ is $C_1$–$C_2$ alkyl and W is nitrogen. Other preferred compounds of IC are those where each $R_a$ is methyl and W is nitrogen.

Other preferred compounds of the invention have Formula II

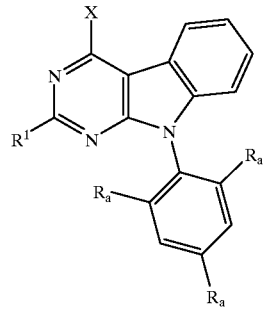

II wherein each $R_a$ independently represents $C_1$–$C_6$ alkyl;

$R^1$ is hydrogen, halogen, trifluoromethyl, $C_1$–$C_6$ alkyl, or ($C_1$–$C_6$ alkyl)-$G^1$—$R^2$ where $G^1$ is oxygen or sulfur and $R^2$ is hydrogen or $C_1$–$C_6$ alkyl;

X is

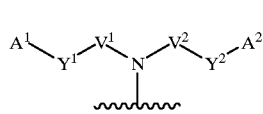

(i)

wherein $V^1$ and $V^2$ are $CH_2$, CO, CS, $SO_2$ or $CH(C_1$–$C_6$ alkyl), with the proviso that both $V^1$ and $V^2$ cannot both be CO, CS or $SO_2$;

$Y^1$ and $Y^2$ independently represent a bond or $C_1$–$C_6$ alkylene;

$A^1$ is $NR^4R^5$ wherein $R^4$ and $R^5$ are independently hydrogen, a lower alkyl group which optionally forms a heterocycloalkyl group with $Y^1$;

$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

lower alkanoyl, lower alkylsulfonyl, with the proviso that $R^4$ and $R^5$ cannot both be alkanoyl or alkylsulfonyl; or $NR^4R^5$ taken together form a $C_3$–$C_6$ heterocycloalkyl or a group of the formula:

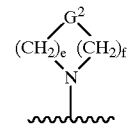

wherein e and f are independently 1, 2 or 3 and the sum of e and f is at least 3; and $G^2$ is $NR^6$ wherein $R^6$ is hydrogen or $C_1$–$C_6$ alkyl, or $CH(C_0$–$C_6$ alkylene)-$G^3$—$R^7$ wherein $G^3$ is CONH, CONH($C_1$–$C_6$ alkyl), NH, NH($C_1$–$C_6$ alkyl) and $R^7$ is hydrogen or $C_1$–$C_6$ alkyl; or $CONH_2$, CO[N($C_1$–$C_6$ alkyl)$R^8$] wherein $R^8$ is hydrogen or $C_1$–$C_6$ alkyl;

$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

$A^2$ is hydrogen, $C_1$–$C_6$ alkyl, ($C_1$–$C_6$ alkylene)-$G^4$—$R^9$ wherein $G^4$ is oxygen or sulfur and $R^9$ is hydrogen, trifluoromethyl or $C_1$–$C_6$ alkyl;

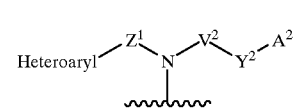

(ii)

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or disubstituted with halogen, trifluoromethyl, amino, $C_1$–$C_6$ alkyl, $C_1$–$C_6$ alkoxy, with the proviso that tetrazolyl can have at most one substituent;

$Z^1$ is $C_1$–$C_6$ alkyl; and $V^2$, $Y^2$ and $A^2$ are as defined above;

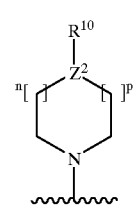

(iii)

where $Z^2$ is carbon or nitrogen;

where when $Z^2$ is CH, n is 0, 1, 2 or 3 and p is 1, 2, or 3, $R^{10}$ is carboxamido, or ($C_0$–$C_6$ alkylene)-$G^5$—$R^{11}$ wherein $G^5$ is NH, NH($C_1$–$C_6$ alkyl)

and R[11] is hydrogen, $C_1$–$C_6$ alkyl, $C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

when $Z^2$ is carbon, n is 1 or 2 and p is 1 or 2, $R^{10}$ is amino; or when $Z^2$ is nitrogen, n is 1 or 2 and p is 1 or 2, $R^{10}$ is hydrogen; or (iv) a nitrogen heterocycle of the formula:

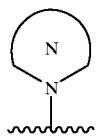

wherein the N-ring represents triazolyl, tetrazolyl, imidazolyl, or pyrazolyl, each of which is optionally substituted with amino, trifluoromethyl, carboxamido, or ($C_1$–$C_6$ alkylene)-$G^6$—$R^{12}$ wherein $G^6$ is NH, NH($C_1$–$C_6$ alkyl) and $R^{12}$ is hydrogen, $C_1$–$C_1$ alkyl, $C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring.

Preferred compounds of Formula II are those where $V^1$ and $V^2$ represent methylene; $Y^1$ is a bond; $A^1$ represents pyrrolidinyl, morpholinyl; piperazinyl, mono- or di-$C_1$–$C_6$ alkyl, $C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring; $Y^2$ represents a bond or methylene; and $A^2$ represents $C_1$–$C_6$ alkyl or $C_1$–$C_6$ alkoxymethyl.

Other preferred compounds of the invention have Formula III

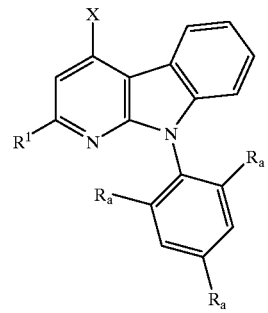

wherein
each $R_a$ independently represents $C_1$–$C_6$ alkyl;
$R^1$ is hydrogen, halogen, trifluoromethyl, $C_1$–$C_6$ alkyl, or ($C_1$–$C_6$ alkyl)-$G^1$—$R^2$ where $G^1$ is oxygen or sulfur and $R^2$ is hydrogen or $C_1$–$C_6$ alkyl; and
X is

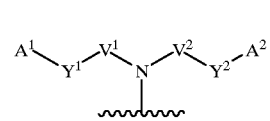

$V^1$ and $V^2$ are $CH_2$, CO, CS, $SO_2$ or CH($C_1$–$C_6$ alkyl), with the proviso that both $V^1$ and $V^2$ cannot both be CO, CS or $SO_2$;

$Y^1$ and $Y^2$ independently represent a bond or $C_1$–$C_6$ alkylene;

$A^1$ is $NR^4R^5$ wherein $R^4$ and $R^5$ are independently hydrogen, a lower alkyl group which optionally forms a heterocycloalkyl group with $Y^1$;

$C_1$–$C_6$ arylalkyl or $C_1$–$C_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl,1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

lower alkanoyl, lower alkylsulfonyl, with the proviso that $R^4$ and $R^5$ cannot both be alkanoyl or alkylsulfonyl; or $NR^4R^5$ taken together form a $C_3$–$C_6$ heterocycloalkyl or a group of the formula:

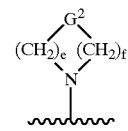

wherein e and f are independently 1, 2 or 3 and the sum of e and f is at least 3; and
$G^2$ is
$NR^6$ wherein $R^6$ is hydrogen or $C_1$–$C_6$ alkyl, or CH($C_0$–$C_6$ alkylene)-$G^3$—$R^7$ wherein $G^3$ is CONH, CONH(C$_1$–C$_6$ alkyl), NH, NH(C$_1$–C$_6$ alkyl) and R$^7$ is hydrogen or C$_1$–C$_6$ alkyl; or CONH$_2$, CO[(N(C$_1$–C$_6$ alkyl)R$^8$] wherein R$^8$ is hydrogen or C$_1$–C$_6$ alkyl;

C$_1$–C$_6$ arylalkyl or C$_1$–C$_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

A$^2$ is hydrogen, C$_1$–C$_6$ alkyl, (C$_1$–C$_6$ alkylene)-G$^4$—R$^9$ wherein G$^4$ is oxygen or sulfur and R$^9$ is hydrogen, trifluoromethyl or C$_1$–C$_6$ alkyl;

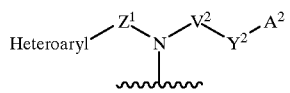

(ii)

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or disubstituted with halogen, trifluoromethyl, amino, C$_1$–C$_6$ alkyl, C$_1$–C$_6$ alkoxy, with the proviso that tetrazolyl can have at most one substituent;

Z$^1$ is C$_1$–C$_6$ alkyl; and
V$^2$, Y$^2$ and A$^2$ are as defined above;

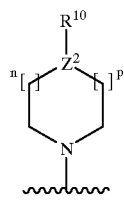

(iii)

where
Z$^2$ is carbon or nitrogen;
where
when Z$^2$ is CH, n is 0, 1, 2 or 3-and p is 1, 2, or 3, R$^{10}$ is carboxamido, or (C$_0$–C$_6$ alkylene)-G$^5$—R$^{11}$ wherein G$^5$ is NH, NH(C$_1$–C$_6$ alkyl) and R$^{11}$ is hydrogen, C$_1$–C$_6$ alkyl, C$_1$–C$_6$ arylalkyl or C$_1$–C$_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;
when Z$^2$ is carbon, n is 1 or 2 and p is 1 or 2, R$^{10}$ is amino; or
when Z$^2$ is nitrogen, n is 1 or 2 and p is 1 or 2, R$^{10}$ is hydrogen; or (iv) a nitrogen heterocycle of the formula:

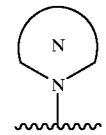

wherein the N-ring represents triazolyl, tetrazolyl, imidazolyl, or pyrazolyl, each of which is optionally substituted with amino, trifluoromethyl, carboxamido, or (C$_1$–C$_6$ alkylene)-G$^6$—R$^{12}$ wherein G$^6$ is NH, NH(C$_1$–C$_6$ alkyl) and R$^{12}$ is hydrogen, C$_1$–C$_6$ alkyl, C$_1$–C$_6$ arylalkyl or C$_1$–C$_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring.

Preferred compounds of Formula III are those where V$^1$ and V$^2$ represent methylene; Y$^1$ is a bond; A$^1$ represents pyrrolidinyl, morpholinyl; piperazinyl, mono- or di-C$_1$–C$_6$ alkyl, C$_1$–C$_6$ arylalkyl or C$_1$–C$_6$ heteroarylalkyl, where aryl is phenyl, and heteroaryl is 2-,3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring; Y$^2$ represents a bond or methylene; and A$^2$ represents C$_1$–C$_6$ alkyl or C$_1$–C$_6$ alkoxymethyl.

Preferred compounds of the invention include:

4-(N-(2-N',N'-Dimethylaminoethyl)-N-ethyl)amino-2-methyl-9-(4-bromo-2,6-dimethylphenyl)-9H-pyrimidino[4,5-b]indole 4-(N-(2-N',N'-Dimethylaminoethyl)-N-propyl)amino-2-methyl-9-(2,4,6-trimethylphenyl)-9H-pyridino[2,3-b]indole 4-(N-(2-N',N'-Dimethylaminoethyl)-N-2-methoxyethyl) amino-2-methyl-9-(2,4,6-trimethylphenyl)-9H-pyridino[2,3-b]indole 4-(N-(2-N',N'-Dimethylaminoethyl)-N-cyclopropylmethyl)amino-2-methyl-9-(2,4,6-trimethylphenyl)-9H-pyridino[2,3-b]indole 4-(N-(2-Pyrrolidinoethyl)-N-cyclopropylmethyl)amino-2-methyl-9-(2,4,6-trimethylphenyl)-9H-pyridino[2,3-b]indole 4-(N-(2-N'-Ethylaminoethyl)-N-cyclopropylmethyl) amino-2-methyl-9-(2,4,6-trimethylphenyl)-9H-pyridino[2,3-b]indole 4-(N-(2-N'-Ethyl-N'-methylaminoethyl)-N-cyclopropylmethyl)amino-2-methyl-9-(2,4,6-trimethylphenyl)-9H-pyridino[2,3-b]indole 4-(N-(2-N',N'-Dimethylaminoethyl)-N-cyclopropylmethyl)amino-2-methyl-9-(4-methoxy-2-methylphenyl)-9H-pyridino[2,3-b]indole 4-(N-(2-N',N'-Diethylaminoethyl)-N-cyclopropylmethyl)amino-2-methyl-9-(2,4,6-trimethylphenyl)-9H-pyridino[2,3-b]indole 4-(N-(2-N'-Methylaminoethyl)-N-cyclopropylmethyl)amino-2-methyl-9-(2,4,6-trimethylphenyl)-9H-pyridino[2,3-b]indole 4-(N-(2-Aminoethyl)-N-cyclopropylmethyl)amino-2-methyl-9-(2,4,6-trimethylphenyl)-9H-pyridino[2,3-b]indole 4-(N-(2-Piperidinoethyl)-N-cyclopropylmethyl)amino-2-methyl-9-(2,4,6-trimethylphenyl)-9H-pyridino[2,3-b]indole 4-(N-(2-Pyrrolidinoethyl)-N-propyl)amino-2-methyl-9-(2,4,6-trimethylphenyl)-9H-pyridino[2,3-b]indole 4-(N-(2-Piperidinoethyl)-N-propyl)amino-2-methyl-9-(2,4,6-trimethylphenyl)-9H-pyridino[2,3-b]indole 4-(N-(2-Morpholinoethyl)-N-cyclopropylmethyl)amino-2-methyl-9-(2,4,6-trimethylphenyl)-9H-pyridino[2,3-b]indole 4-(N-(2-N'-Ethyl-N'-methylaminoethyl)-N-propyl)amino-2-methyl-9-(2,4,6-trimethylphenyl)-9H-pyridino[2,3-b]indole 4-(N-(2-N',N'-Dimethylaminoethyl)-N-cyclopropylmethyl)amino-2-methyl-9-(2,4,6-trimethylphenyl)-9H-pyrimidino[4,5-b]indole 4-(N-(2-(1-Imidazolyl)ethyl)-N-cyclopropylmethyl)amino-2-methyl-9-(2,4,6-trimethylphenyl)-9H-pyridino[2,3-b]indole 4-(N-(2-Pyrrolidinoethyl)-N-1-oxopropyl)amino-2-methyl-9-(2,4,6-trimethylphenyl)-9H-pyridino[2,3-b]indole 4-(N-(2-Pyrrolidinoethyl)-N-cyclopropyloxomethyl)amino-2-methyl-9-(2,4,6-trimethylphenyl)-9H-pyridino[2,3-b]indole 4-(N-2-(N'-Methylpiperazinyl)ethyl-N-cyclopropylmethyl)-amino-2-methyl-9-(2,4,6-trimethylphenyl)-9H-pyridino[2,3-b]indole 4-(N-(2-Pyridylmethyl)-N-cyclopropylmethyl)amino-2-methyl-9-(2,4,6-trimethylphenyl)-9H-pyridino[2,3-b]indole 4-Piperazinyl-2-methyl-9-(2,4,6-trimethylphenyl)-9H-pyridino[2,3-b]indole 4-(N-(2-Aminoethyl)-N-propyl)amino-2-methyl-9-(2,4,6-trimethylphenyl)-9H-pyridino[2,3-b]indole 4-(N-(2-Aminoethyl)-N-ethyl)amino-2-methyl-9-(2,4,6-trimethylphenyl)-9H-pyridino[2,3-b]indole 4-(N-(2-(4-Triazolyl)ethyl)-N-cyclopropylmethyl)amino-2-methyl-9-(2,4,6-trimethylphenyl)-9H-pyridino[2,3-b]indole 4-(N-(2-Pyrrolidinoethyl)-N-cyclopropylmethyl)amino-2-methyl-9-(2,4-dimethylphenyl)-9H-pyridino[2,3-b]indole 4-(N-(3-Pyrrolidinoproyl)-N-cyclopropylmethyl)amino-2-methyl-9-(2,4,6-trimethylphenyl)-9H-pyridino[2,3-b]indole 4-(N-(2-(2-Phenethylamino)ethyl)-N-cyclopropylmethyl)amino-2-methyl-9-(2,4,6-trimethylphenyl)-9H-pyridino[2,3-b]indole 4-(N-(2-Pyrrolidinoethyl)-N-cyclopropylmethyl)amino-2-methyl-9-(2,4,6-trimethylphenyl)-9H-pyrimidino[4,5-b]indole 4-(N-(2-Pyrrolidinoethyl)-N-2-methoxyethyl)amino-2-methyl-9-(2,4,6-trimethylphenyl)-9H-pyridino[2,3-b]indole 4-(N-(2-Pyrrolidinoethyl)-N-ethyl)amino-2-methyl-9-(2,4,6-trimethylphenyl)-9H-pyridino[2,3-b]indole 4-(N-(2-Pyrrolidinoethyl)-N-butyl)amino-2-methyl-9-(2,4,6-trimethylphenyl)-9H-pyridino[2,3-b]indole 4-(N-(2-Pyrrolidinoethyl)-N-2-methylpropyl)amino-2-methyl-9-(2,4,6-trimethylphenyl)-9H-pyridino[2,3-b]indole 4-(N-(2-Carboxamidoethyl)-N-cyclopropylmethyl)amino-2-methyl-9-(2,4,6-trimethylphenyl)-9H-pyridino[2,3-b]indole 4-(N-(2-Pyrrolidinoethyl)-N-cyclopropylmethyl)amino-2-methyl-9-(4-bromo-2,6-dimethylphenyl)-9H-pyrimidino[4,5-b]indole 4-(N-(2-N',N'-Dimethylaminoethyl)-N-2-methylpropyl)amino-2-methyl-9-(2,4,6-trimethylphenyl)-9H-pyridino[2,3-b]indole 4-(N-(2-N'-Ethyl-N'-methylaminoethyl)-N-2-methylpropyl)amino-2-methyl-9-(2,4,6-trimethylphenyl)-9H-pyridino[2,3-b]indole 4-(N-(2-N',N'-Dimethylaminooethyl)-N-propyl)amino-2-methyl-9-(2,4,6-trimethylphenyl)-9H-pyrimidino[4,5-b]indole 4-(N-(2-N',N'-Dimethylaminooethyl)-N-butyl)amino-2-methyl-9-(2,4,6-trimethylphenyl)-9H-pyrimidino[4,5-b]indole 4-(N-(2-N',N'-Dimethylaminooethyl)-N-cyclopropyl)amino-2-methyl-9-(2,4,6-trimethylphenyl)-9H-pyrimidino[4,5-b]indole 4-(N-(2-(1-Methyl-2-pyrrolidino)ethyl)-N-cyclopropylmethyl)amino-2-methyl-9-(2,4,6-trimethylphenyl)-9H-pyridino[2,3-b]indole 4-(N-(2-N',N'-Dimethylaminoethyl)-N-cyclobutyl)amino-2-methyl-9-(2,4,6-trimethylphenyl)-9H-pyrimidino[4,5-b]indole 4-(N-(2-N',N'-Dimethylaminoethyl)-N-isopropyl)amino-2-methyl-9-(2,4,6-trimethylphenyl)-9H-pyrimidino[4,5-b]indole 4-(N-(2-Pyrrolidinoethyl)-N-isopropyl)amino-2-methyl-9-(2,4,6-trimethylphenyl)-9H-pyrimidino[4,5-b]indole 4-(N-(2-N',N'-Dimethylaminoethyl)-N-isopropyl)amino-2-methyl-9-(2,4,6-trimethylphenyl)-9H-pyrimidino[4,5-b]indole In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)$n-COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "alkyl", "lower alkyl", or $C_1$–$C_6$ alkyl in the present invention is meant straight or branched chain alkyl groups having 1–6 carbon atoms optionally forming a 3 to 6 atoms carbocycle, such as, for example, methyl, ethyl, propyl, isopropyl, cyclopropyl, cyclopropylmethyl, n-butyl, sec-butyl, tert-butyl, cyclobutyl, pentyl, 2-pentyl, isopentyl, neopentyl, cyclopentyl, hexyl, 2-hexyl, 3-hexyl, 3-methylpentyl, cyclohexyl.

By $C_0$–$C_6$ alkylene is meant a direct bond or a $C_1$–$C_6$ alkylene group, optionally forming a 3 to 6 atoms carbocycle, such as methylene, ethylidene, propylidene, butylidene, pentylidene, cyclopentylidene, hexylidene, cyclohexylidene.

By "alkoxy", "lower alkoxy", or $C_1$–$C_6$ alkoxy in the present invention is meant straight or branched chain alkoxy groups having 1–6 carbon atoms optionally forming a 3 to 6 atoms carbocycle, such as, for example, methoxy, ethoxy, propoxy, isopropoxy, cyclopropylmethoxy, n-butoxy, sec-butoxy, tert-butoxy, pentoxy, 2-pentoxy, isopentoxy, neopentoxy, cyclopentoxy, hexoxy, 2-hexoxy, 3-hexoxy, 3-methylpentoxy, cyclohexoxy.

By "alkanoyl", "lower alkanoyl", or $C_1$–$C_6$ alkanoyl as used herein is meant straight or branched chain alkanoyl groups having 1–6 carbon atoms optionally forming a 3 to 6 atom carbocycle, such as, for example, acetyl, propionyl, isopropionyl, cyclopropionyl, butanoyl, pentanoyl, cyclopentanoyl, hexanoyl, cyclhexanoyl. The "ω-position" of the alkanoyl groups herein is the terminal carbon atom.

CONH represents an amide functional group, i.e.,

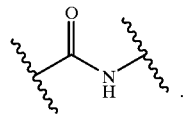

The term "heterocycle" or "heterocycloalkyl" means a monocyclic or bicyclic hydrocarbon group which in which one or more of the ring carbon atoms has been replaced with a heteroatom, e.g., oxygen, sulfur or nitrogen. Such groups preferably have 4 to 10 carbon atoms and 1 to 4 heteroatoms.

By the term "halogen" in the present invention is meant fluorine, bromine, chlorine, and iodine.

Representative aminoalkyl substituted 9H-pyridino[2,3-b]indole and 9H-pyrimidino[4,5-b]indole derivatives of the present invention, which are encompassed by Formula I, include, but are not limited to the compounds in Examples 1–18 and their pharmaceutically acceptable addition salts.

The interaction of aminoalkyl substituted 9H-pyridino[2,3-b]indole and 9H-pyrimidino[4,5-b]indole derivatives of the invention with $CRF_1$ and $NPY_1$ receptors is shown in the examples. This interaction results in the pharmacological activities of these compounds as illustrated in relevant animal models.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachid oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachid oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 Ümg to about 140 Ümg per kilogram of body weight per day are useful in the treatment of the above-indicated conditions (about 0.5 Ümg to about 7Üg per patient per day). The amount of active ingredient that may be combined with the carrier materials to produce a single dosage form will vary depending upon the host treated and the particular mode of administration. Dosage unit forms will generally contain between from about 1 Ümg to about 500 Ümg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preparation of Aminoalkyl Substituted 9H-Pyridino [2,3-b]indole and 9H-Pyrimidino[4,5-b]indole Analogues An illustration of the preparation of compounds of the present invention is given in Scheme I, Scheme II and Scheme III. Those having skill in the art will recognize that the starting materials may be varied and additional steps employed to produce compounds encompassed by the present invention.

Scheme I

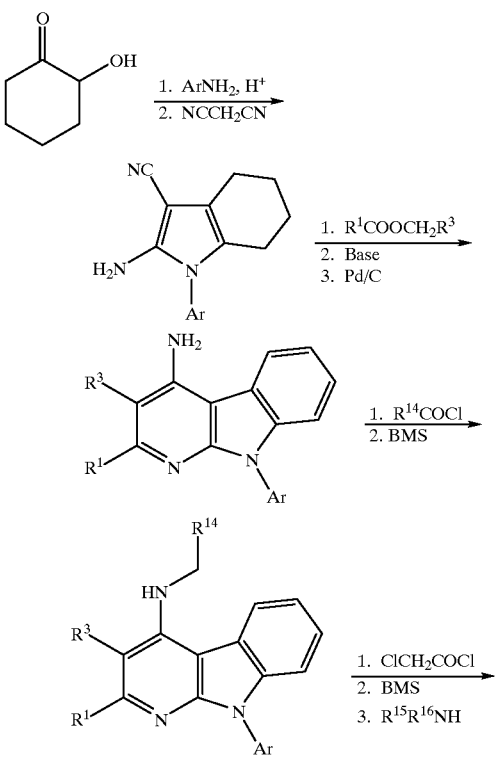

23

-continued

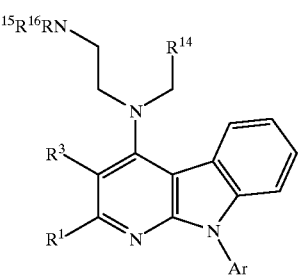

wherein Ar, $R^1$ and $R^1$ are as defined above for Formula I; and $R^{14}$, $R^{15}$ and $R^{16}$ are encompassed by the definition of X as defined in Formula I.

Scheme II

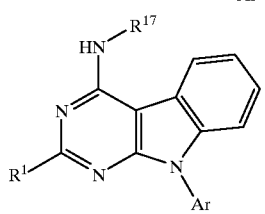

wherein Ar, $R^1$ and $R^2$ are as defined above for Formula I; and $R^{15}$ and $R^{16}$ are encompassed by the definition of X as defined in Formula I.

Scheme III

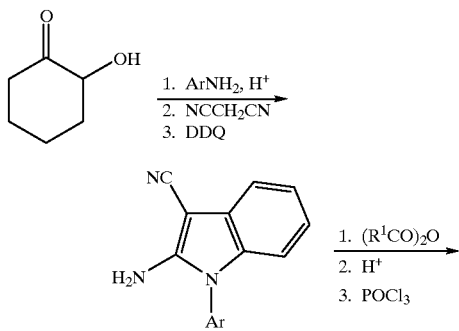

24

-continued

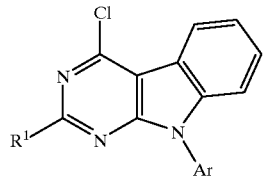

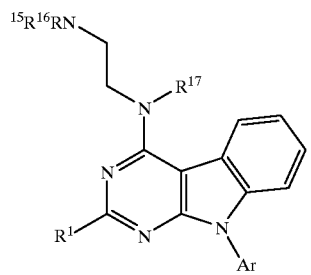

wherein Ar and $R^1$ are as defined as above for Formula I; and $R^{15}$, $R^{16}$ and $R^{17}$ are encompassed by the definition of X as defined in Formula I.

The disclosures of all articles and references mentioned in this application, including patents, are incorporated herein by reference.

The preparation of the compounds of the present invention is illustrated further by the following Examples, which are not to be construed as limiting the invention in scope or spirit to the specific procedures and compounds described in them.

Commercial reagents were used without further purification. THF refers to tetrahydrofuran. LDA refers to lithium diisopropylamide and DDQ refers to 2,3-dichloro-5,6-dicyano-1,4-benzoquinone. Room or ambient temperature refers to 20 to 25° C. Concentration implies the use of a rotary evaporator. TLC refers to thin layer chromatography. Mass spectral data were obtained either by CI or APCI methods.

EXAMPLE 1

A. 2-Amino-4,5,6,7-tetrahydro-1-phenyl-1H-indole-3-carbonitrile

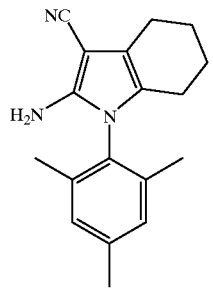

A mixture of 2,4,6-trimethylaniline (500 g) and adipoin (464 g) in toluene (2.5 L) is heated to reflux. A theoretical amount of water is removed azeotropically over the course of 3 hours. The mixture is cooled to ambient temperature, then malononitrile (244 g) and ammonium acetate (57 g) are added. The reaction is slowly re-heated back to reflux for about 1 hour with azeotropic removal of water. After cooling, the precipitate that forms overnight is collected by filtration. The dark solid is washed with ethanol and dried to afford 540 g of a white powder: MS 280 (M+H).

B. 4-Amino-2-methyl-9-(2,4,6-trimethylphenyl)-5,6,7,8-tetrahydro-9H-pyridino[2,3-b]indole

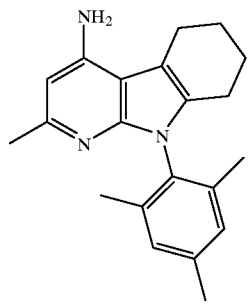

To the product of Example 1A (535 g) dissolved in dichloroethane (4 L) are added 2-methoxypropene (550 mL) and p-toluenesulfonic acid monohydrate (3.6 g). The mixture is refluxed for 1 hour then the solvent is removed by distillation. The residue is dissolved in THF (3 L) and cooled to 0° C. To this solution, under an atmosphere of nitrogen gas, is added LDA (2.0M, 1.2 L) at a rate to keep the reaction's internal temperature below 10° C. After 3 hours the reaction is neutralized with aqueous HCl. The aqueous layer is extracted with ethyl acetate and combined with the THF layer. The combined organic phase is extracted with 3M HCl and the latter is made alkaline (pH=10) with 10N NaOH and ice. The aqueous solution is extracted with dichloromethane, dried with sodium sulfate, filtered and concentrated to give a crystalline solid: MS 320 (M+H).

C. 4-Amino-2-methyl-9-(2,4,6-trimethylphenyl)-9H-pyridino[2,3-b]indole

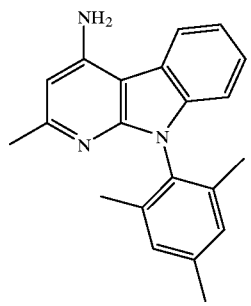

The product of Example 1B (600 g) is dissolved in decahydronaphthalene (4 L) and heated to distill off low boiling impurities that are present. The solution is cooled to ambient temperature and charged with 10% Palladium on Carbon (250 g) under a blanket of argon gas. The mixture is heated to the reflux temperature of 191–193° C. for 9 hours to afford aromatized product. The cooled mixture is diluted with dichloromethane and filtered through a pad of celite. The dichloromethane in the filtrate is removed under reduced vacuum. The remaining decahydronaphthalene solution is treated by bubbling in a stream of hydrochloric acid gas with ice-cooling for about 5 minutes. The solids are filtered, washed with diethyl ether and dried to yield 580 g of product as the HCl salt. The salt is recrystallized from an ethyl acetate and ethanol mixture to give a white product: MS(free base) 316 (M+H).

D. 4-(N-Cyclopropylmethyl)amino-2-methyl-9-(2,4,6-trimethylphenyl)-9H-pyridino[2,3-b]indole

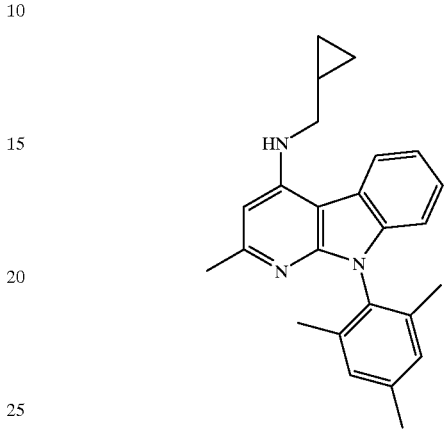

A solution of dichloroethane (250 mL) containing the product of Example 1C (50 g as HCl salt) and cyclopropanecarbonyl chloride (14 mL) at reflux is treated with dropwise addition of N,N-diisopropylethylamine (54 mL) After heating for 0.5 hour the reaction is cooled to ambient temperature and poured into aqueous potassium carbonate solution. The product is extracted with dichloromethane, dried over sodium sulfate, filtered and concentrated to give a white solid. This solid is re-dissolved in THF (600 mL) and mixed with borane-methyl sulfide complex (10M, 43 mL). The mixture is heated to reflux for 8 hours and quenched at room temperature with a large excess of methanol (about 200 mL). Re-heat mixture to reflux for 1 hour, then concentrate under reduced pressure. More methanol (another 200 mL) is added to the gummy residue and the solution is re-concentrated to yield a white solid: MS 370 (M+H).

E. 4-(N-(2-Chloroethyl)-N-cyclopropylmethyl)amino-2-methyl-9-(2,4,6-trimethylphenyl)-9H-pyridino[2,3-b]indole

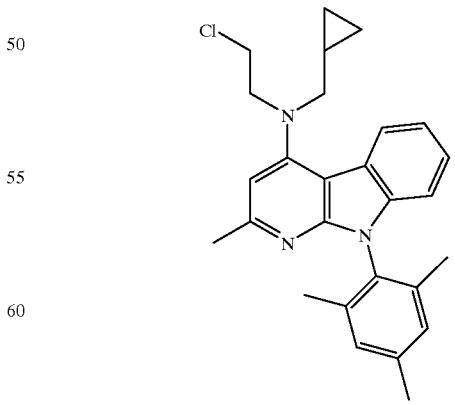

A solution containing the product from Example 1D (52 g) and chloroacetyl chloride (34 mL) in dichloroethane (500 mL) is refluxed for 4 hours. The solvent and excess reagent are removed under reduced pressure. Aqueous potassium carbonate is added to the remaining oily residue and extracted with dichloromethane. The extract is dried with sodium sulfate, filtered and concentrated. The latter chloroacetyl compound (63 g) is dissolved in THF (250 mL). Add borane-methyl sulfide complex (10M, 14 mL) and stir at ambient temperature for 15 minutes then for 1 hour at reflux temperature. The solution is cooled back to room temperature, quenched with a large excess of methanol (100 mL) and re-heated to reflux for 1 hour. The solution is concentrated to give a viscous oil that crystallizes on standing: MS 432 (M+H).

F. 4-(N-(2-Pyrrolidinoethyl)-N-cyclopropylmethyl) amino-2-methyl-9-(2,4,6-trimethylphenyl)-9H-pyridino[2,3-b]indole (Compound 1)

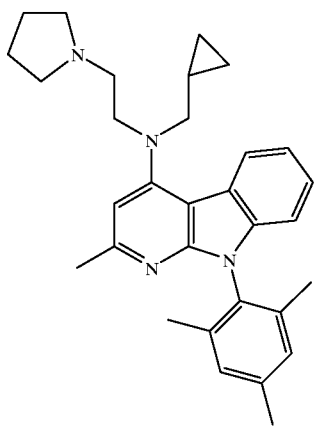

A steel bomb containing the product from Example 1E (61 g) pyrrolidine (60 mL) and N-methylpyrrolidinone (250 mL) is sealed and heated to 120° C. for 5 hours. The mixture is poured into water and extracted with ethyl acetate. The organic layer is washed with water, dried over sodium sulfate, filtered and concentrated. The product is purified by flash chromatography. First 100% ethyl acetate is used to elute impurities followed by 10% methanol in dichloromethane to elute the desired product. Obtain 60 g of compound that crystallizes on standing. The sulfate salt of the amine is formed by adding concentrated sulfuric acid (2.44 mL) to amine (21.4 g) dissolved in ethanol (50 mL). Isopropanol (200 mL) is added to the ethanol solution at reflux. Crystals of sulfate that form on cooling are collected by filtration and washed with cold isopropanol: MS(free base) 467 (M+H).

G. 4-Propylamino-2-methyl-9-(2,4,6-trimethylphenyl)-9H-pyridino[2,3-b]indole

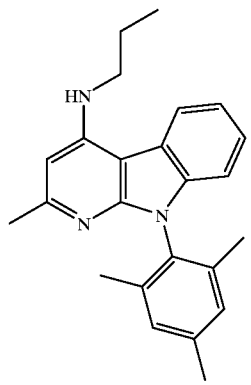

An excess of sodium borohydride (about 1 g) is added in small portions to a propionic acid (10 mL) solution of the product from Example 1C (1.4 g). After gas evolution ceases the reaction is heated to 100° C. for 0.5. hour. Propionic acid is removed from the mixture under reduced pressure and crude product is extracted from aqueous potassium carbonate with dichloromethane. The dichloromethane extract is dried over sodium sulfate, filtered and concentrated: MS 358 (M+H).

H. 4-Cyclopropylamino-2-methyl-9-(2,4,6-trimethylphenyl)-9H-pyridino[2,3-b]indole

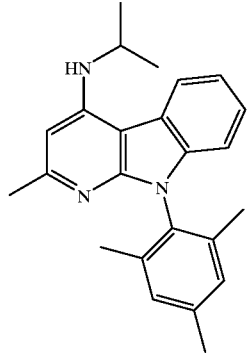

To a solution of the product from Example 1C (10 g) and 2-methoxypropene (50 mL) in dichloroethane (100 mL) is added acetic acid (1.6 mL) and sodium triacetoxyborohydride (25 g). The mixture is stirred at room temperature for 24 hours then concentrated. Dissolve residue in ethyl acetate and wash with water, followed by 1N sodium hydroxide and brine. Dry over sodium sulfate, filter and concentrate: MS 358 (M+H).

EXAMPLE 2

The following compounds are prepared essentially according to the procedures set forth above in Example 1.

a) 4-(N-(2-N',N'-Dimethylaminoethyl)-N-propyl)amino-2-methyl-9-(2,4,6-trimethylphenyl)-9H-pyridino[2,3-b]indole: MS 429 (M+H). (Compound 2)
b) 4-(N-(2-N',N'-Dimethylaminoethyl)-N-2-methoxyethyl)amino-2-methyl-9-(2,4,6-trimethylphenyl)-9H-pyridino[2,3-b]indole: MS 445 (M+H). (Compound 3)
c) 4-(N-(2-N',N'-Dimethylaminoethyl)-N-cyclopropylmethyl)amino-2-methyl-9-(2,4,6-trimethylphenyl)-9H-pyridino[2,3-b]indole: MS 441 (M+H). (Compound 4)
d) 4-(N-(2-N'-Ethylaminoethyl)-N-cyclopropylmethyl)amino-2-methyl-9-(2,4,6-trimethylphenyl)-9H-pyridino[2,3-b]indole: MS 441 (M+H). (Compound 5)
e) 4-(N-(2-(N'-Ethyl-N'-methyl)aminoethyl)-N-cyclopropylmethyl)amino-2-methyl-9-(2,4,6-trimethylphenyl)-9H-pyridino[2,3-b]indole: MS 455 (M+H). (Compound 6)
f) 4-(N-2-(2-(S)-Methoxymethylpyrrolidino)ethyl-N-cyclopropylmethyl)amino-2-methyl-9-(2,4,6-trimethylphenyl)-9H-pyridino[2,3-b]indole: MS 511 (M+H). (Compound 7)
g) 4-(N-(2-N',N'-Dimethylaminoethyl)-N-cyclopropylmethyl)amino-2-methyl-9-(4-methoxy-2-methylphenyl)-9H-pyridino[2,3-b]indole: MS 443 (M+H). (Compound 8)
h) 4-(N-(2-N',N'-Diethylaminoethyl)-N-cyclopropylmethyl)amino-2-methyl-9-(2,4,6-trimethylphenyl)-9H-pyridino[2,3-b]indole: MS 469 (M+H). (Compound 9)
i) 4-(N-(2-N'-Methylaminoethyl)-N-cyclopropylmethyl)amino-2-methyl-9-(2,4,6-trimethylphenyl)-9H-pyridino[2,3-b]indole: MS 427 (M+H). (Compound 10)
j) 4-(N-(2-Piperidinoethyl)-N-cyclopropylmethyl)amino-2-methyl-9-(2,4,6-trimethylphenyl)-9H-pyridino[2,3-b]indole: MS 481 (M+H). (Compound 11)
k) 4-(N-(2-Pyrrolidinoethyl)-N-propyl)amino-2-methyl-9-(-2,4,6-trimethylphenyl)-9H-pyridino[2,3-b]indole: MS 455 (M+H). (Compound 12)
l) 4-(N-(2-Piperidinoethyl)-N-propyl)amino-2-methyl-9-(2,4,6-trimethylphenyl)-9H-pyridino[2,3-b]indole: MS 469 (M+H). (Compound 13)
m) 4-(N-(2-Morpholinoethyl)-N-cyclopropylmethyl)amino-2-methyl-9-(2,4,6-trimethylphenyl)-9H-pyridino[2,3-b]indole: MS 483 (M+H). (Compound 14)
n) 4-(N-(2-N'-Ethyl-N l-methylaminoethyl)-N-propyl)amino-2-methyl-9-(2,4,6-trimethylphenyl)-9H-pyridino[2,3-b]indole: MS 443 (M+H). (Compound 15)
o) 4-(N-(2-(1-Imidazolyl)ethyl)-N-cyclopropylmethyl)amino-2-methyl-9-(2,4,6-trimethylphenyl)-9H-pyridino[2,3-b]indole: MS 464 (M+H). (Compound 16)
p) 4-(N-2-(N'-Methylpiperazinyl)ethyl-N-cyclopropylmethyl)amino-2-methyl-9-(2,4,6-trimethylphenyl)-9H-pyridino[2,3-b]indole: MS 496 (M+H). (Compound 17)
q) 4-(N-2-(N'-Methylhomopiperazinyl)ethyl-N-cyclopropylmethyl)amino-2-methyl-9-(2,4,6-trimethylphenyl)-9H-pyridino[2,3-b]indole: MS 510 (M+H). (Compound 18)
r) 4-(N-(2-N'-Isopropylaminoethyl)-N-cyclopropylmethyl)amino-2-methyl-9-(2,4,6-trimethylphenyl)-9H-pyridino[2,3-b]indole: MS 454 (M+H). (Compound 19)
s) 4-(N-(2-(2-(1-Methyl-2-pyrrolidino)ethyl)aminoethyl)-N-cyclopropylmethyl)amino-2-methyl-9-(2,4,6-trimethylphenyl)-9H-pyridino[2,3-b]indole: MS 524 (M+H). (Compound 20)
t) 4-(N-(2-Piperazinylethyl)-N-cyclopropylmethyl)amino-2-methyl-9-(2,4,6-trimethylphenyl)-9H-pyridino[2,3-b]indole: MS 482 (M+H). (Compound 21)
u) 4-(N-(2-Pyrrolidinoethyl)-N-cyclopropylmethyl)amino-2-methyl-9-(2,4-dimethylphenyl)-9H-pyridino[2,3-b]indole: MS 453 (M+H). (Compound 22)
v) 4-(N-(3-Pyrrolidinoproyl)-N-cyclopropylmethyl)amino-2-methyl-9-(2,4,6-trimethylphenyl)-9H-pyridino[2,3-b]indole: MS 481 (M+H). (Compound 23)
w) 4-(N-(2-Methyl-2-pyrrolidinoethyl)-N-cyclopropylmethyl)amino-2-methyl-9-(2,4,6-trimethylphenyl)-9H-pyridino[2,3-b]indole: MS481 (M+H). (Compound 24)
x) 4-(N-(4-Pyrrolidinobutyl)-N-cyclopropylmethyl)amino-2-methyl-9-(2,4,6-trimethylphenyl)-9H-pyridino [2,3-b]indole: MS 495 (M+H). (Compound 25)
y) 4-(N-(2-(4-Piperidinopiperidinyl)ethyl)-N-cyclopropylmethyl)amino-2-methyl-9-(2,4,6-trimethylphenyl)-9H-pyridino[2,3-b]indole: MS 564 (M+H). (Compound 26)
z) 4-(N-(2-(2-Phenethylamino)ethyl)-N-cyclopropylmethyl)amino-2-methyl-9-(2,4,6-trimethylphenyl)-9H-pyridino[2,3-b]indole: MS 517 (M+H). (Compound 27)
aa) 4-(N-(2-N'-Methylaminoethyl)-N-methyl)amino-2-methyl-9-(2,4,6-trimethylphenyl)-9H-pyridino[2,3-b]indole: MS 387 (M+H). (Compound 28)
bb) 4-(N-(2-Pyrrolidinoethyl)-N-2-methoxyethyl)amino-2-methyl-9-(2,4,6-trimethylphenyl)-9H-pyridino[2,3-b]indole: MS 471 (M+H). (Compound 29)
cc) 4-(N-(2-Pyrrolidinoethyl)-N-ethyl)amino-2-methyl-9-(2,4,6-trimethylphenyl)-9H-pyridino[2,3-b]indole: MS 441 (M+H). (Compound 30)
dd) 4-(N-(2-Pyrrolidinoethyl)-N-butyl)amino-2-methyl-9-(2,4,6-trimethylphenyl)-9H-pyridino[2,3-b]indole: MS 469 (M+H). (Compound 31)
ee) 4-(N-(2-Pyrrolidinoethyl)-N-2-methylpropyl)amino-2-methyl-9-(2,4,6-trimethylphenyl)-9H-pyridino[2,3-b]indole: MS 469 (M+H). (Compound 32)
ff) 4-(N-(2-N',N'-Dimethylaminoethyl)-N-2-methylpropyl)amino-2-methyl-9-(2,4,6-trimethylphenyl)-9H-pyridino[2,3-b]indole: MS 443 (M+H). (Compound 33)
gg) 4-(N-(2-(N'-Ethyl-N l-methyl)aminoethyl)-N-2-methylpropyl)amino-2-methyl-9-(2,4,6-trimethylphenyl)-9H-pyridino[2,3-b]indole: MS 457 (M+H). (Compound 34)
hh) 4-(N-(2-Pyrrolidinoethyl)-N-isopropyl)amino-2-methyl-9-(2,4,6-trimethylphenyl)-9H-pyridino[2,3-b]indole: MS 455 (M+H). (Compound 35)
ii) 4-(N-(2-N',N'-Dimethylaminoethyl)-N-isopropyl)amino-2-methyl-9-(2,4,6-trimethylphenyl)-9H-pyridino[2,3-b]indole: MS 429 (M+H). (Compound 36)
jj) 4-(N-(2-Guanidinoethyl)-N-cyclopropylmethyl)amino-2-methyl-9-(2,4,6-trimethylphenyl)-9H-pyrimidino[4,5-b]indole: MS 455 (M+H). (Compound 37)

kk) 4-(N-(2-(2-(4-Methoxy)phenethylamino)ethyl)-N-ethyl)amino-2-methyl-9-(2,4,6-trimethylphenyl)-9H-pyridino[2,3-b]indole: MS 521 (M+H). (Compound 38)

ll) 4-(N-(2-N'-Cyclopentylaminoethyl)-N-ethyl)amino-2-methyl-9-(2,4,6-trimethylphenyl)-9H-pyridino[2,3-b]indole: MS 455 (M+H). (Compound 39)

mm) 4-(N-(2-N',N'-Dimethylaminoethyl)-N-ethyl)amino-2-methyl-9-(2,4,6-trimethylphenyl)-9H-pyridino[2,3-b]indole: MS 415 (M+H). (Compound 40)

nn) 4-(N-(2-N',N'-Dimethylaminoethyl)-N-cyclopropylmethyl)amino-2-methyl-9-(2,6-dimethylphenyl)-9H-pyridino[2,3-b]indole: MS 427 (M+H). (Compound 41)

EXAMPLE 3

4-(N-(2-aminoethyl)-N-cyclopropylmethyl)amino-2-methyl-9-(2,4,6-trimethylphenyl)-9H-pyridino[2,3-b]indole (Compound 42)

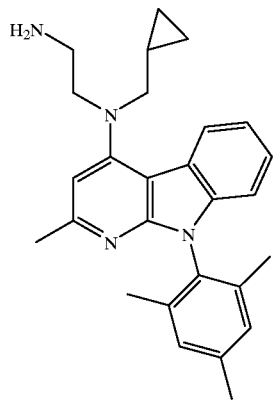

A solution of the product from Example 1E (900 mg) and sodium azide (410 mg) in N-methylpyrrolidinone (10 mL) is heated to 120° C. for 2 hours. The mixture is poured into water and extracted with ethyl acetate. The organic layer is washed with water, dried over sodium sulfate, filtered and concentrated. An ethanol (10 mL) solution of the crude product and 10% palladium on carbon (about 300 mg) is hydrogenated for 8 hours at approximately 1 atmosphere pressure. The suspension is filtered over celite and the concentrated product is purified by flash chromatography, then converted to the hydrochloride salt: MS(free base) 413 (M+H). (Compound 42)

The following compounds are prepared essentially according to the procedure set forth in Example 3.

a) 4-(N-(3-Aminopropyl)-N-cyclopropylmethyl)amino-2-methyl-9-(2,4,6-trimethylphenyl)-9H-pyridino[2,3-b]indole: MS 427 (M+H). (Compound 43)

b) 4-(N-(2-Amino-2-methylethyl)-N-cyclopropylmethyl)amino-2-methyl-9-(2,4,6-trimethylphenyl)-9H-pyridino[2,3-b]indole: MS 427 (M+H). (Compound 44)

c) 4-(N-(2-Aminoethyl)-N-propyl)amino-2-methyl-9-(2,4,6-trimethylphenyl)-9H-pyridino[2,3-b]indole: MS 401 (M+H). (Compound 45)

d) 4-(N-(2-Aminoethyl)-N-cyclopropylmethyl)amino-2-methyl-9-(2,4-dimethylphenyl)-9H-pyridino[2,3-b]indole: MS 399 (M+H). (Compound 46)

e) 4-(N-(2-Aminoethyl)-N-cyclopropylmethyl)amino-2-methyl-9-(2,6-dimethylphenyl)-9H-pyridino[2,3-b]indole: MS 399 (M+H). (Compound 47)

f) 4-(N-(2-Aminoethyl)-N-ethyl)amino-2-methyl-9-(2,4,6-trimethylphenyl)-9H-pyridino[2,3-b]indole: MS 387 (M+H). (Compound 48)

g) 4-(N-(4-Aminobutyl)-N-cyclopropylmethyl)amino-2-methyl-9-(2,4,6-trimethylphenyl)-9H-pyridino[2,3-b]indole: MS 441 (M+H). (Compound 49)

EXAMPLE 4

4-(N-(2-(4-Triazolyl)ethyl)-N-cyclopropylmethyl)amino-2-methyl-9-(2,4,6-trimethylphenyl)-9H-pyridino[2,3-b]indole (Compound 50)

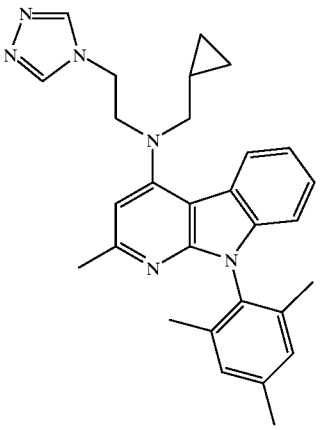

A solution containing the product from Example 3 (380 mg) in toluene (8 mL) with N,N'-dimethylformamide azine (195 mg) and p-toluenesulfonic acid monohydrate (6 mg) is heated at reflux. A flowing stream of nitrogen gas is used to displace evolving dimethylamine. After 12 hours heating is discontinued and the solution is diluted with ethyl acetate and washed with water, brine and dried over sodium sulfate, filtered and concentrated to a tan colored solid. The product is purified by preparative TLC using 7% methanol and 0.1% ammonium hydroxide in dichloromethane as eluent to afford 340 mg of product: MS 465 (M+H).

EXAMPLE 5

4-(N-(2-Carboxamidoethyl)-N-cyclopropylmethyl) amino-2-methyl-9-(2,4,6-trimethylphenyl)-9H-pyridino[2,3-b]indole (Compound 51)

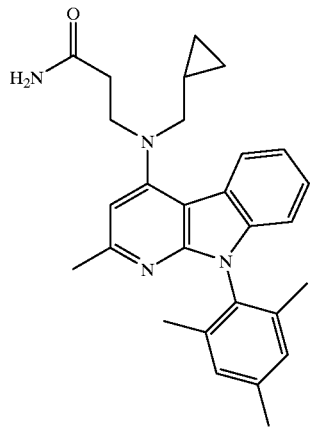

Dissolve the compound from Example 3 (1.0 g) and sodium cyanide (540 mg) in N-methylpyrrolidinone (20 mL) and heat to 95° C. for 2 hours. The mixture is poured into water and extracted with ethyl acetate. The organic layer is washed with water, dried over sodium sulfate, filtered and concentrated. Purify by flash chromatography using 20% ethyl acetate in hexanes to yield a white solid. Dissolve nitrile (130 mg) and solid sodium hydroxide (800 mg) in tert-butanol (5 mL). Reflux mixture for about 1 hour. Next, neutralize with 6N hydrochloric acid, concentrate and purify residue by preparative TLC using 10% methanol in dichloromethane as eluent: MS 441 (M+H).

EXAMPLE 6

4-(N-(2-N'-acetyl-N'-methylaminoethyl)-N-cyclopropylmethyl)amino-2-methyl-9-(2,4,6-trimethylphenyl)-9H-pyridino[2,3-b]indole (Compound 53)

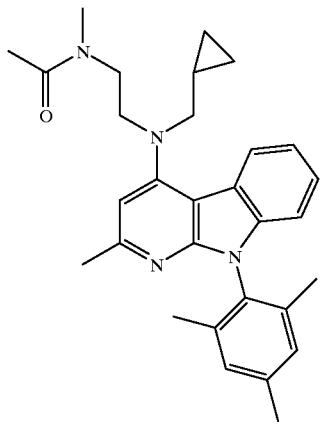

To a solution of the compound from Example 2i (170 mg) in dichloromethane (5 mL) is added acetic anhydride (0.1 mL) and diisopropylethylamine (0.2 mL). The solution is stirred for 0.5 hour then concentrated. The residue is dissolved in ethyl acetate, washed with sodium carbonate and water, dried over sodium sulfate, filtered and concentrated. The product is purified by preparative TLC using 70% ethyl acetate in hexanes as eluent: MS 469 (M+H).

EXAMPLE 7

The following compounds are prepared essentially according to the procedures set forth above in Example 6.

a) 4-(N-(2-(N'-Methanesulfonyl-N'-methylamino)ethyl)-N-cyclopropylmethyl)amino-2-methyl-9-(2,4,6-trimethylphenyl)-9H-pyridino[2,3-b]indole: MS 505 (M+H). (Compound 54)

b) 4-(N-(2-(N'-Methyl-N'-trifluoromethanesulfonyl) aminoethyl)-N-cyclopropylmethyl)amino-2-methyl-9-(2,4,6-trimethylphenyl)-9H-pyridino[2,3-b]indole: MS 559 (M+H). (Compound 55)

c) 4-(N-(2-(4-Aminophenylsulfonamido)ethyl)-N-cyclopropylmethyl)amino-2-methyl-9-(2,4,6-trimethylphenyl)-9H-pyridino[2,3-b]indole: MS 568 (M+H). (Compound 56)

d) 4-(N-(2-(2-Thienylsulfonamido)ethyl)-N-cyclopropylmethyl)amino-2-methyl-9-(2,4,6-trimethylphenyl)-9H-pyridino[2,3-b]indole: MS 559 (M+H). (Compound 57)

e) 4-(N-(2-(2-(2-Thienyl)-1-oxoethyl)aminoethyl)-N-cyclopropylmethyl)amino-2-methyl-9-(2,4,6-trimethylphenyl)-9H-pyridino[2,3-b]indole: MS 537 (M+H). (Compound 58)

f) 4-(N-(2-(2-Phenyl-1-oxoethyl)aminoethyl)-N-cyclopropylmethyl)amino-2-methyl-9-(2,4,6-trimethylphenyl)-9H-pyridino[2,3-b]indole: MS 531 (M+H). (Compound 59)

EXAMPLE 8

4-(N-(2-N',N'-dimethylamino-1-oxoethyl)-N-cyclopropylmethyl)amino-2-methyl-9-(2,4,6-trimethylphenyl)-9H-pyridino[2,3-b]indole (Compound 60)

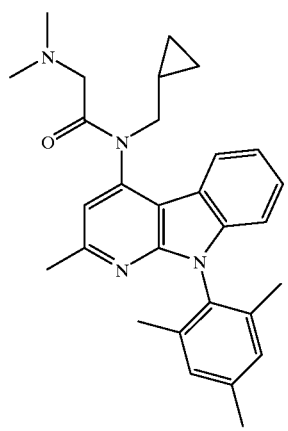

Refrigerated dimethylamine (about 4 mL) is poured into a solution of the chloroacetyl compound from Example 1E (1.9 g) and acetonitrile (20 mL). The reaction vessel is sealed and the mixture is stirred at ambient temperature for 2 hours then concentrated. Water is added to the residue and the aqueous is extracted with ethyl acetate. The extract is dried over sodium sulfate, filtered and concentrated. The product is purified on preparative TLC with 100% ethyl acetate as the eluting solvent: MS 443 (M+H).

EXAMPLE 9

The following compounds are prepared essentially according to the procedure set forth in Example 8.

a) 4-(N-(2-N',N'-Dimethylamino-1-oxoethyl)-N-propyl) amino-2-methyl-9-(2,4,6-trimethylphenyl)-9H-pyridino[2,3-b]indole: MS 443 (M+H). (Compound 61)

b) 4-(N-(2-N',N'-Dimethylamino-1-oxoethyl)-N-2-methoxyethyl)amino-2-methyl-9-(2,4,6-trimethylphenyl)-9H-pyridino[2,3-b]indole: MS 459 (M+H). (Compound 62)

c) 4-(N-(2-Pyrrolidino-1-oxoethyl)-N-cyclopropylmethyl)amino-2-methyl-9-(2,4,6-trimethylphenyl)-9H-pyridino[2,3-b]indole: MS 481 (M+H). (Compound 63)

d) 4-(N-(2-N'-Ethylamino-1-oxoethyl)-N-cyclopropylmethyl)amino-2-methyl-9-(2,4,6-trimethylphenyl)-9H-pyridino[2,3-b]indole: MS 455 (M+H). (Compound 64)

e) 4-(N-(2-(N'-Ethyl-N 1-methyl)amino-1-oxoethyl)-N-cyclopropylmethyl) amino-2-methyl-9-(2,4,6-trimethylphenyl)-9H-pyridino[2,3-b]indole: MS 469 (M+H). (Compound 65)

f) 4-(N-(2-(2-(S)-Methoxymethylpyrrolidino)-1-oxoethyl)-N-cyclopropylmethyl)amino-2-methyl-9-(2,4,6-trimethylphenyl)-9H-pyridino[2,3-b]indole: MS 525 (M+H). (Compound 66)

g) 4-(N-(2-(1-Imidazolyl)-1-oxoethyl)-N-cyclopropylmethyl)amino-2-methyl-9-(2,4,6-trimethylphenyl)-9H-pyridino[2,3-b]indole: MS 478 (M+H). (Compound 67)

EXAMPLE 10

A. 4-(N-(2-Chloro-1-oxoethyl)-N-propyl)amino-2-methyl-9-(2,4,6-trimethylphenyl)-9H-pyridino[2,3-b]indole

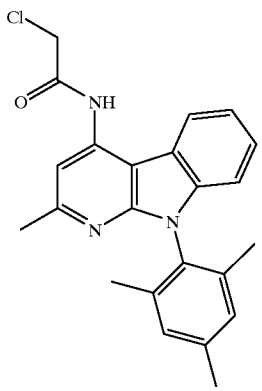

A solution of the compound from Example 1C (5.7 g), chloroacetyl chloride (3 mL) and diisopropylethylamine (3 mL) in dichloroethane (90 mL) is refluxed for 0.5 hour. After concentrating the mixture, aqueous potassium carbonate is added and product is extracted with dichloromethane. The extract is dried over sodium sulfate, filtered and concentrated. The chloride (1.0 g) is dissolved in acetonitrile (20 mL) and mixed with pyrrolidine (2 mL). The solution is stirred for 2 hours at ambient temperature then concentrated. Water is added to the residue and the aqueous is extracted with ethyl acetate. The extract is dried over sodium sulfate, filtered and concentrated: MS 392 (M+H).

B. 4-(N-(2-pyrrolidinoethyl)-N-1-oxopropyl)amino-2-methyl-9-(2,4,6-trimethylphenyl)-9H-pyridino[2,3-b]indole (Compound 68)

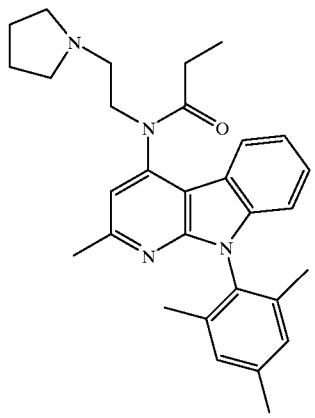

To a solution of the compound from Example 10A (1.0 g) in acetonitrile (25 mL) is added pyrrolidine (1.0 mL). The solution is stirred at room temperature for 2 hours then concentrated. Water is added to the residue and the aqueous is extracted with ethyl acetate. The extract is dried over sodium sulfate, filtered and concentrated. The isolated aminoamide (1.1 g) is dissolved in THF (25 mL), treated with borane-methyl sulfide complex(10M, 1.0 mL) and refluxed for 8 hours. The solution is cooled and quenched with an excess of methanol (25 mL). Next, N,N 1-dimethylethylenediamine (1.1 mL) is added and the mixture is re-heated to reflux for 4 hours. The solution is concentrated, diluted with ethyl acetate, washed with water, dried over sodium sulfate, filtered and concentrated. To a solution containing the latter product (330 mg), diisopropylethylamine (0.2 mL) and dichloroethane (10 mL) is added propionyl chloride (0.1 mL). The mixture is refluxed for 0.5 hour, then poured into aqueous potassium carbonate and extracted with ethyl acetate. The extract is dried over sodium sulfate, filtered and concentrated. The product is purified on preparative TLC with 10% methanol in dichloromethane as the eluting solvent: 469 (M+H).

EXAMPLE 11

The following compounds are prepared essentially according to the procedure set forth in Example 10.

a) 4-(N-(2-Pyrrolidinoethyl)-N-cyclopropyloxomethyl) amino-2-methyl-9-(2,4,6-trimethylphenyl)-9H-pyridino[2,3-b]indole: MS 481 (M+H). (Compound 69)

b) 4-(N-(2-Dimethylaminoethyl)-N-methoxymethyloxomethyl)amino-2-methyl-9-(2,4,6-trimethylphenyl)-9H-pyridino[2,3-b]indole: MS 459 (M+H). (Compound 70)

EXAMPLE 12

4-(N-(2-pyridylmethyl)-N-cyclopropylmethyl)amino-2-methyl-9-(2,4,6-trimethylphenyl)-9H-pyridino[2,3-b]indole (Compound 71)

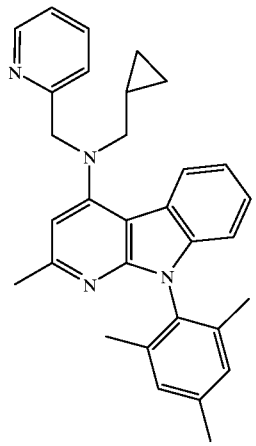

A solution of the compound from Example 1D (110 mg), picolinyl chloride (98 mg) and N,N-diisopropylethylamine in DMF (5 mL) is stirred at 60° C. for 12 hours. The mixture is poured into water and extracted with ethyl acetate. The extract is washed with water, dried over sodium sulfate, filtered and concentrated. The product is purified by preparative TLC using 30% ethyl acetate in hexanes as eluent: MS 461 (M+H).

EXAMPLE 13

The following compounds are prepared essentially according to the procedure of Example 12.

a) 4-(N-(2-N',N'-Dimethylamino-2-oxoethyl)-N-2-methoxyethyl)amino-2-methyl-9-(2,4,6-trimethylphenyl)-9H-pyridino[2,3-b]indole: MS 459 (M+H). (Compound 72)

b) 4-(N-(2-N',N'-Dimethylamino-2-oxoethyl)-N-propyl)amino-2-methyl-9-(2,4,6-trimethylphenyl)-9H-pyridino[2,3-b]indole: MS 443 (M+H). (Compound 73)

c) 4-(N-(2-N',N'-Dimethylamino-2-oxoethyl)-N-2-methoxy-1-oxoethyl)amino-2-methyl-9-(2,4,6-trimethylphenyl)-9H-pyridino[2,3-b]indole: MS 473 (M+H). (Compound 74)

d) 4-(N-(2-N',N'-Dimethylamino-1-oxoethyl)-N-cyclopropylmethyl)amino-2-methyl-9-(2,4,6-trimethylphenyl)-9H-pyridino[2,3-b]indole: MS 455 (M+H). (Compound 75)

EXAMPLE 14

4-(4-Triazolyl)-2-methyl-9-(2,4,6-trimethylphenyl)-9H-pyridino[2,3-b]indole (Compound 76)

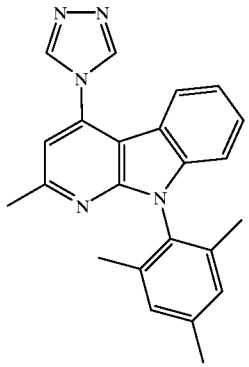

A solution containing the compound from Example 1C (560 mg) in toluene (10 mL) with N,N'-dimethylformamide azine (400 mg) and p-toluenesulfonic acid monohydrate (50 mg) is heated at reflux. A flowing stream of nitrogen gas is used to displace evolving dimethylamine. After 24 hours heating is discontinued and the solution is diluted with ethyl acetate and washed with water, brine and dried over sodium sulfate, filtered and concentrated to a tan colored solid. The product is purified by preparative TLC using 100% ethyl acetate as eluent to afford 340 mg of product: MS 368 (M+H).

EXAMPLE 15

A. 4-Chloro-2-methyl-9-(2,4,6-trimethylphenyl)-9H-pyridino[2,3-b]indole

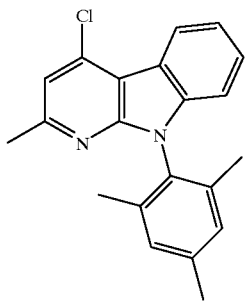

Dissolve tert-butylnitrite (0.65 g) in acetonitrile (10 mL) and add copper(II)chloride (0.68 g). Then the compound from Example 1C (1.33 g) is added portionwise to the greenish-brown solution and the mixture is stirred for 12 hours. The acetonitrile is removed by evaporation and the residue is partitioned between water and dichloromethane. The aqueous layer is extracted with more dichloromethane and the combined extract is washed with water, dried over sodium sulfate, filtered and concentrated. The product is filtered through a plug of silica gel using 20% ethyl acetate in hexanes as eluent to afford a tan colored solid: MS 335 (M+H).

B. 4-Piperazinyl-2-methyl-9-(2,4,6-trimethylphenyl)-9H-pyridino[2,3-b]indole (Compound 77)

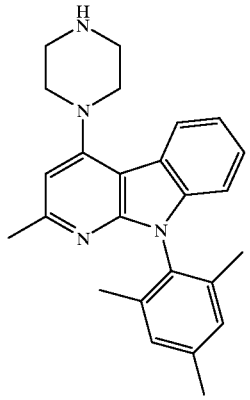

Combine the compound from Example 15A (200 mg) and piperazine (0.58 g) in N-methylpyrrolidinone (2 mL) and heat the solution to 120° C. for 12 hours. Pour mixture into water and extract with ethyl acetate. Wash extract with aqueous ammonium chloride then water. Dry extract over sodium sulfate, filter and concentrate. Purify by preparative TLC using 10% methanol in dichloromethane as eluent: MS 385 (M+H).

EXAMPLE 16

The following compounds are prepared essentially according to the procedures set forth above in Example 15.

a) 4-(4-Methylpiperazinyl)-2-methyl-9-(2,4,6-trimethylphenyl)-9H-pyridino[2,3-b]indole: MS 399 (M+H). (Compound 78)

b) 4-Homopiperazinyl-2-methyl-9-(2,4,6-trimethylphenyl)-9H-pyridino[2,3-b]indole: MS 399 (M+H). (Compound 79)

c) 4-(N-(2-(1-Methyl-2-pyrrolidino)ethyl)-N-cyclopropylcarbonyl)amino-2-methyl-9-(2,4,6-trimethylphenyl)-9H-pyridino[2,3-b]indole: MS 495 (M+H). (Compound 80)

d) 4-(N-2-(S)-Pyrrolidinomethylpyrrolidinyl)-2-methyl-9-(2,4,6-trimethylphenyl)-9H-pyridino[2,3-b]indole: MS 453 (M+H). (Compound 81)

e) 4-(4-Aminomethylpiperidino)-2-methyl-9-(2,4,6-trimethylphenyl)-9H-pyridino[2,3-b]indole: MS 413 (M+H). (Compound 82)

f) 4-(4-Piperidinopiperidinyl)-2-methyl-9-(2,4,6-trimethylphenyl)-9H-pyridino[2,3-b]indole: MS 467 (M+H). (Compound 83)

g) 4-(4-Carboxamidopiperidinyl)-2-methyl-9-(2,4,6-trimethylphenyl)-9H-pyridino[2,3-b]indole: MS 427 (M+H). (Compound 84)

h) 4-(3-Aminopyrrolidinyl)-2-methyl-9-(2,4,6-trimethylphenyl)-9H-pyridino[2,3-b]indole: MS 385 (M+H). (Compound 85)

i) 4-(N-(2-(1-Methyl-2-pyrrolidino)ethyl)-N-cyclopropylmethyl)amino-2-methyl-9-(2,4,6-trimethylphenyl)-9H-pyridino[2,3-b]indole: MS 481 (M+H). (Compound 86)

j) 4-(N-2-(S)-Cyclopentylaminomethylpyrrolidinyl)-2-methyl-9-(2,4,6-trimethylphenyl)-9H-pyridino[2,3-b]indole: MS 467 (M+H). (Compound 87)

k) 4-(N-2-(R)-Cyclopentylaminomethylpyrrolidinyl)-2-methyl-9-(2,4,6-trimethylphenyl)-9H-pyridino[2,3-b]indole: MS 467 (M+H). (Compound 88)

l) 4-(N-3-Cyclopentylaminopyrrolidinyl)-2-methyl-9-(2,4,6-trimethylphenyl)-9H-pyridino[2,3-b]indole: MS 467 (M+H). (Compound 89)

m) 4-(N-3-(2-(3-Methoxy-4-ethoxy)phenethyl)aminopyrrolidinyl)-2-methyl-9-(2,4,6-trimethylphenyl)-9H-pyridino[2,3-b]indole: MS 563 (M+H). (Compound 90)

n) 4-(N-3-(1-oxo-2-(3-Methoxy-4-ethoxy)phenethyl)aminopyrrolidinyl)-2-methyl-9-(2,4,6-trimethylphenyl)-9H-pyridino[2,3-b]indole: MS 577 (M+H). (Compound 91)

o) 4-(N-2-(2-(R)-(4-Methoxy)phenethyl)aminomethylpyrrolidinyl)-2-methyl-9-(2,4,6-trimethylphenyl)-9H-pyridino[2,3-b]indole: MS 533 (M+H). (Compound 92)

p) 4-(N-2-(2-(S)-(4-Methoxy)phenethyl)aminomethylpyrrolidinyl)-2-methyl-9-(2,4,6-trimethylphenyl)-9H-pyridino[2,3-b]indole: MS 533 (M+H). (Compound 93)

q) 4-(N-4-(2-(3-Methoxy-4-ethoxy)phenethyl)aminomethylpiperazinyl)-2-methyl-9-(2,4,6-trimethylphenyl)-9H-pyridino[2,3-b]indole: MS 563 (M+H). (Compound 94)

EXAMPLE 17

A. 2-Amino-1-phenyl-1H-indole-3-carbonitrile

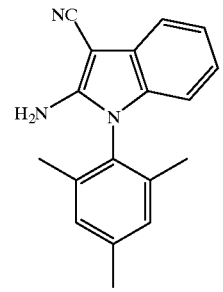

Dissolve the compound from Example 1A (20 g) in 1,4-dioxane (300 mL) and add DDQ (34 g) portionwise to the solution. The reaction is stirred for 1 hour then filtered through celite to remove insoluble side products. The filtrate is concentrated and allowed to solidify. The product is collected by filtration and washed with ethanol to yield 16 g of a tan colored powder: MS 276 (M+H).

B. 4-Hydroxy-2-methyl-9-(2,4,6-trimethylphenyl)-9H-pyrimidino[4,5-b]indole

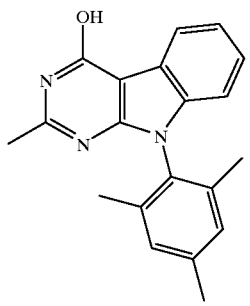

A mixture of the compound from Example 12A (30 g), acetic anhydride (15 mL) and acetic acid (30 mL) is refluxed for 1 hour then, concentrated to a solid. Phosphoric acid (40 mL, 85%) is added to the amide. The mixture is then refluxed for 0.5 hour and cooled to ambient temperature. The solution is poured onto ice and the precipitate that forms is collected by filtration. The solids are washed with water and some ethanol: MS 318 (M+H).

C. 4-Chloro-2-methyl-9-(2,4,6-trimethylphenyl)-9H-pyrimidino[4,5-b]indole

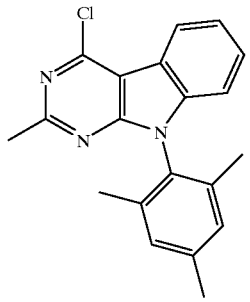

The compound from Example 12B (2.2 g) is refluxed in phosphoryl chloride (30 mL) for 3 hours. The excess phosphoryl chloride is removed under reduced pressure and the residue is partitioned between aqueous potassium carbonate and dichloromethane. The aqueous is extracted with more dichloromethane. The combined extracts are dried over sodium sulfate, filtered and concentrated to give a tan colored solid: MS 336 (M+H).

D. 4-Cyclopropylamino-2-methyl-9-(2,4,6-trimethylphenyl)-9H-pyrimidino[4,5-b]indole

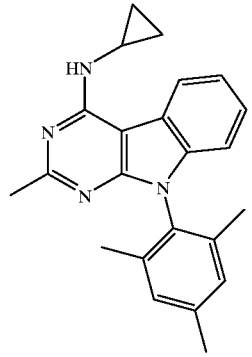

A mixture of the compound from Example 12C (750 mg) and cyclopropylamine (1.6 mL) in N-methylpyrrolidinone (2 mL) is heated to 65° C. in a sealed tube for 24 hours. Dilute mixture with ethyl acetate and wash with water, brine, dry over sodium sulfate, filter and concentrate to give a tan colored solid. Purify by radial chromatography using 40% ethyl acetate in hexanes as eluent to give 730 mg of product: MS 357 (M+H).

E. 4-(N-(2-N',N'-Dimethylaminooethyl)-N-cyclopropyl)amino-2-methyl-9-(2,4,6-trimethylphenyl)-9H-pyrimidino[4,5-b]indole (Compound 95)

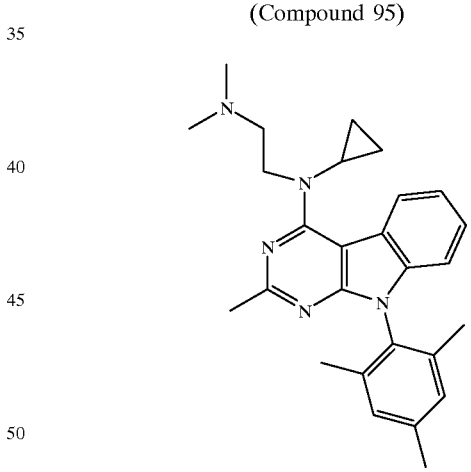

To a solution of compound from Example 12D (200 mg) in dimethylformamide (5 mL) at 0° C., under a blanket of nitrogen, is added sodium hydride (60%, 100 mg). After stirring the solution for 15 minutes, 2-dimethylaminoethyl chloride hydrochloride (170 mg) is added. The mixture is then heated to 60° C. for 2 hours, then quenched with ice and water. Diluted with ethyl acetate and washed with water, brine, dried over sodium sulfate, filtered and concentrated. Purified by radial chromatography using 7% methanol and 0.5% ammonium hydroxide in dichloromethane as eluent to obtain 190 mg of product: MS 428 (M+H).

EXAMPLE 18

The following compounds are prepared essentially according to the procedure of Example 17.

a) 4-(N-(2-N',N'-Dimethylaminoethyl)-N-methyl)amino-2-methyl-9-(2,4,6-trimethylphenyl)-9H-pyrimidino[4,5-b]indole: MS 466 (M+H). (Compound 96)

b) 4-(N-(2-N',N'-Dimethylaminoethyl)-N-ethyl)amino-2-methyl-9-(4-bromo-2,6-dimethylphenyl)-9H-pyrimidino[4,5-b]indole: MS 480 (M+H). (Compound 97)

c) 4-(N-(2-N',N'-Dimethylaminoethyl)-N-ethyl)amino-2-methyl-9-(4-clhoro-2-methylphenyl)-9H-pyrimidino[4,5-b]indole: MS 422 (M+H). (Compound 98)

d) 4-(N-(2-Morpholinoethyl)-N-propyl)amino-2-methyl-9-(2-chloro-4-methylphenyl)-9H-pyrimidino[4,5-b]indole: MS 478 (M+H). (Compound 99)

e) 4-(N-(2-N',N'-Dimethylaminoethyl)-N-cyclopropylmethyl)amino-2-methyl-9-(2,4,6-trimethylphenyl)-9H-pyrimidino[4,5-b]indole: MS 442 (M+H). (Compound 100)

f) 4-Piperazinyl-2-methyl-9-(2,4,6-trimethylphenyl)-9H-pyrimidino[4,5-b]indole: MS 386 (M+H). (Compound 101)

g) 4-(N-(2-Pyrrolidinoethyl)-N-cyclopropylmethyl)amino-2-methyl-9-(2,4,6-trimethylphenyl)-9H-pyrimidino[4,5-b]indole: MS 468 (M+H). (Compound 102)

h) 4-(3-Aminopyrrolidinyl)-2-methyl-9-(2,4,6-trimethylphenyl)-9H-pyrimidino[4,5-b]indole: MS 386 (M+H). (Compound 103)

i) 4-(2-(S)-Aminomethylpyrrolidino)-2-methyl-9-(2,4,6-trimethylphenyl)-9H-pyrimidino[4,5-b]indole: MS 400 (M+H). (Compound 104)

j) 4-(3-Amino-2-triazolyl)-2-methyl-9-(2,4,6-trimethylphenyl)-9H-pyrimidino[4,5-b]indole: MS 384 (M+H). (Compound 105)

k) 4-(3-Amino-1-triazolyl)-2-methyl-9-(2,4,6-trimethylphenyl)-9H-pyrimidino[4,5-b]indole: MS 384 (M+H). (Compound 106)

l) 4-(3-Amino-4-triazolyl)-2-methyl-9-(2,4,6-trimethylphenyl)-9H-pyrimidino[4,5-b]indole: MS 384 (M+H). (Compound 107)

m) 4-(N-(2-Pyrrolidinoethyl)-N-cyclopropylmethyl)amino-2-methyl-9-(4-bromo-2,6-dimethylphenyl)-9H-pyrimidino[4,5-b]indole: MS 532 (M+H). (Compound 108)

n) 4-(N-(2-Pyrrolidinoethyl)-N-propyl)amino-2-methyl-9-(2,4,6-trimethylphenyl)-9H-pyrimidino[4,5-b]indole: MS 456 (M+H). (Compound 109)

o) 4-(N-(2-Pyrrolidinoethyl)-N-butyl)amino-2-methyl-9-(2,4,6-trimethylphenyl)-9H-pyrimidino[4,5-b]indole: MS 470 (M+H). (Compound 110)

p) 4-(N-(2-Pyrrolidinoethyl)-N-cyclopropyl)amino-2-methyl-9-(2,4,6-trimethylphenyl)-9H-pyrimidino[4,5-b]indole: MS 454 (M+H). (Compound 111)

q) 4-(N-(2-N',N'-Dimethylaminooethyl)-N-propyl)amino-2-methyl-9-(2,4,6-trimethylphenyl)-9H-pyrimidino[4,5-b]indole: MS 430 (M+H). (Compound 112)

r) 4-(N-(2-N',N'-Dimethylaminoethyl)-N-butyl)amino-2-methyl-9-(2,4,6-trimethylphenyl)-9H-pyrimidino[4,5-b]indole: MS 444 (M+H). (Compound 113)

s) 4-(N-(2-Piperidinoethyl)-N-propyl)amino-2-methyl-9-(2,4,6-trimethylphenyl)-9H-pyrimidino[4,5-b]indole: MS 470 (M+H). (Compound 114)

t) 4-(N-(2-Piperidinoethyl)-N-butyl)amino-2-methyl-9-(2,4,6-trimethylphenyl)-9H-pyrimidino[4,5-b]indole: MS 484 (M+H). (Compound 115)

u) 4-(N-(2-N',N'-Dimethylaminoethyl)-N-cyclobutyl)amino-2-methyl-9-(2,4,6-trimethylphenyl)-9H-pyrimidino[4,5-b]indole: MS 442 (M+H). (Compound 116)

v) 4-(N-(2-N',N'-Dimethylaminoethyl)-N-cyclopentyl)amino-2-methyl-9-(2,4,6-trimethylphenyl)-9H-pyrimidino[4,5-b]indole: MS 456 (M+H). (Compound 117)

w) 4-(N-(2-N',N'-Dimethylaminoethyl)-N-isopropyl)amino-2-methyl-9-(2,4,6-trimethylphenyl)-9H-pyrimidino[4,5-b]indole: MS 430 (M+H). (Compound 118)

x) 4-(N-(2-N'-Methylaminoethyl)-N-methyl)amino-2-methyl-9-(2,4,6-trimethylphenyl)-9H-pyrimidino[4,5-b]indole: MS 388 (M+H). (Compound 119)

y) 4-(4-(N-Methylamino)piperidino)-2-methyl-9-(2,4,6-trimethylphenyl)-9H-pyrimidino[4,5-b]indole: MS 414 (M+H). (Compound 120)

z) 4-(4-(2-Aminoethyl)piperazinyl)-2-methyl-9-(2,4,6-trimethylphenyl)-9H-pyrimidino[4,5-b]indole: MS 429 (M+H). (Compound 121)

aa) 4-(N-(2-N'-Ethylaminoethyl)-N-ethyl)amino-2-methyl-9-(2,4,6-trimethylphenyl)-9H-pyrimidino[4,5-b]indole: MS 416 (M+H). (Compound 122)

bb) (±)-4-(N-(2-N',N'-Dimethylaminoethyl)-N-1-methylpropyl)amino-2-methyl-9-(2,4,6-trimethylphenyl)-9H-pyrimidino[4,5-b]indole: MS 444 (M+H). (Compound 123)

cc) 4-(N-(2-N',N'-Diethylaminoethyl)-N-cyclopropylmethyl)amino-2-methyl-9-(2,4,6-trimethylphenyl)-9H-pyrimidino[4,5-b]indole: MS 470 (M+H). (Compound 124)

dd) 4-(N-(2-N',N'-Diethylaminoethyl)-N-cyclopropyl)amino-2-methyl-9-(2,4,6-trimethylphenyl)-9H-pyrimidino[4,5-b]indole: MS 456 (M+H). (Compound 125)

ee) 4-(N-(2-N',N'-Dimethylaminoethyl)-N-2-methoxyethyl)amino-2-methyl-9-(2,4,6-trimethylphenyl)-9H-pyrimidino[4,5-b]indole: MS 446 (M+H). (Compound 126)

ff) 4-(N-(2-N',N'-Dimethylaminoethyl)-N-2-ethoxyethyl)amino-2-methyl-9-(2,4,6-trimethylphenyl)-9H-pyrimidino[4,5-b]indole: MS 460 (M+H). (Compound 127)

gg) 4-(N-(2-N"-Ethylaminoethyl)-N-ethyl)amino-2-methyl-9-(2-methyl-4-chlorophenyl)-9H-pyrimidino[4,5-b]indole: MS 423 (M+H). (Compound 128)

hh) 4-(N-(Cyclopentylaminopiperidin-4-yl)-N-ethyl)amino-2-methyl-9-(2,4,6-trimethylphenyl)-9H-pyrimidino[4,5-b]indole: MS 468 (M+H). (Compound 129)

ii) 4-(N-(2-N',N'-Dimethylaminoethyl)-N-isobutyl)amino-2-methyl-9-(2,4,6-trimethylphenyl)-9H-pyrimidino[4,5-b]indole: MS 444 (M+H). (Compound 130)

jj) 4-(N-(2-(3-Methoxy-4-ethoxy)phenethyl)aminopiperidin-4-yl)-N-ethyl)amino-2-methyl-9-(2,4,6-trimethylphenyl)-9H-pyrimidino[4,5-b]indole: MS 578 (M+H). (Compound 131)

kk) 4-(N-(S)-(1-Oxo-2-(4-methoxy)phenethyl)aminopyrrolidin-2-yl)-2-methyl-9-(2,4,6- trimethylphenyl)-9H-pyrimidino[4,5-b]indole: MS 54(M+H). (Compound 132)

ll) 4-(N-(S)-(2-(4-Methoxy)phenethyl)aminopyrrolidin-2-yl)-2-methyl-9-(2,4,6-trimethylphenyl)-9H-pyrimidino[4,5-b]indole: MS 578 (M+H). (Compound 133)

EXAMPLE 19

The pharmaceutical utility of compounds of this invention is indicated by the following assays for human CRF1 and NPY1 receptor activity.

Assay for CRF Receptor Binding Activity

CRF receptor binding is performed using a modified version of the assay described by Grigoriadis and De Souza (*Methods in Neurosciences*, Vol. 5, 1991). Membrane pellets containing CRF receptors are re-suspended in 50 mM Tris buffer pH 7.7 containing 10 mM $MgCl_2$ and 2 mM EDTA and centrifuged for 10 minutes at 48000 g. Membranes are washed again and brought to a final concentration of 1500 mg/ml in binding buffer (Tris buffer above with 0.1% BSA, 15 mM bacitracin and 0.01 mg/mL aprotinin). For the binding assay, 100 mL of the membrane preparation is added to 96 well microtube plates containing 100 mL of $^{125}$I-CRF (SA 2200 Ci/mmol, final concentration of 100 pM) and 50 mL of drug. Binding is carried out at room temperature for 2 hours. Plates are then harvested on a Brandel 96 well cell harvester and filters are counted for gamma emissions on a Wallac 1205 Betaplate liquid scintillation counter. Non specific binding is defined by 1 mM cold CRF. $IC_{50}$ values are calculated with the non-linear curve fitting program RS/1 (BBN Software Products Corp., Cambridge, Mass.). The binding affinity for the compounds of Formula I expressed as $IC_{50}$ value, generally ranges from about 0.5 nanomolar to about 10 micromolar.

Alternatively, the binding activity of the compounds of formula I to the human $CRF_1$ receptor can be measured as follows:

Assay for Human CRF Receptor Binding Activity in IMR32 cells

[$^{125}$I]Sauvagine Binding to CRF1 Receptors Endogenously Expressed in IMR-32 Cells: IMR-32 human neuroblastoma cells are grown to 80% confluence in EMEM containing Earle's Balanced Salts and 2 mM 1-glutamine with 10% FBS, 25 mM HEPES, 1 mM Sodium Pyruvate, and nonessential amino acids. At this time, flasks of cells are treated with 2.5 μM 5-bromo-2'-deoxyuridine (Br-dU) for 10 days. Media is changed every 3–4 days across the 10 day period. Cells are harvested using No-Zyme (JRH Biosciences) and rinsed with PBS. For membrane preparation, cells are homogenized in wash buffer (50 mM Tris HCl, 10 mM $MgCl_2$, 2 mM EGTA, pH 7.4) and centrifuged at 48,000×g for 10 minutes at 4° C. Pellets are re-suspended, homogenized and centrifuged two additional times. The receptor binding assay is performed using assay buffer (50 mM Tris HCl, 10 mM $MgCl_2$, 2 mM EGTA, pH 7.4, 0.1% BSA, 0.1 mM bacitracin (22.0 mg/100 mL)), 150 μg protein/tube, and [$^{125}$I]Sauvagine (NEN; 100 pM for competition analysis and 10 pM-1 nM for saturation analysis) to yield a final volume of 200 μL. Nonspecific binding is defined using 2 μM r/h CRF or 9–41 alpha-helical CRF. Cells are incubated for 2 hours at room temperature. The assay is terminated by rapid vacuum filtration (Tomtec: Deepwell 3) through GFC filters presoaked in 1% PEI using ice-cold 50 mM Tris HCl and dry thoroughly by air. Specific Binding: 70–80%; Kd (nM): 0.30 nM; Bmax (fmole/mg protein): 40–50. $IC_{50}$ values are calculated with the non-linear curve fitting program RS/1 (BBN Software Products Corp., Cambridge, Mass.).

The binding affinities for the compounds of Formula I towards the $CRF_1$ receptor are expressed as $IC_{50}$ values and are less than 10 micromolar.

Assay for Human NPY1 Receptor Binding Activity

Compounds are assayed for activity using the following method: Baculovirus-infected Sf9 cells expressing recombinant human NPY Y1 receptors are harvested at 42–48 hours at which time batches of 500 mL of cell suspension are pelleted by centrifugation. Each pellet is re-suspended in 30 mL of lysis buffer (10 mM HEPES, 250 mM sucrose, 0.5 μg/mL leupeptin, 2 μg/mL Aprotonin, 200 μM PMSF and 2.5 mM EDTA, pH 7.4) and gently homogenized by 50 strokes using a dounce homogenizer. The homogenate is centrifuged at 4° C. for 10 minutes at 536×g to pellet the nuclei. The supernatant is collected into a fresh tube and centrifuged twice in the same buffer at 48,000×g for 40 minutes. The final pellet is subsequently re-suspended in 10 mL of PBS containing 5 mM EDTA by dounce homogenization and stored in aliquots at −80° C.

Purified membranes are washed by PBS and re-suspended by gentle pipetting in binding buffer (50 mM Tris(HCl), 5 mM KCl, 120 mM NaCl, 2 mM $CaCl_2$, 1 mM $MgCl_2$, 0.1% bovine serum albumin (BSA), pH 7.4). Membranes (5 μg) are added to siliconized (Sigmacote, Sigma) polypropylene tubes in addition to 0.050 nM [$^{125}$I]NPY(porcine) for competition analysis or 0.010–0.500 nM [$^{125}$I]NPY (porcine) for saturation analysis. For evaluation of guanine nucleotide effects on receptor affinity, GTP is added at a final concentration of 100 μM. Cold displacers are added at concentrations ranging from $10^{-12}$ M to $10^{-6}$ M to yield a final volume of 0.250 mL. Nonspecific binding is determined in the presence of 1 μM NPY (human) and accounts for less than 10% of total binding. Following a 2 hour incubation at room temperature, the reaction is terminated by rapid vacuum filtration. Samples are filtered over presoaked GF/C Whatman filters (1.0% polyethyleneimine for 2 hours) and rinsed 2 times with 5 mL cold binding buffer lacking BSA. Remaining bound radioactivity is measured by gamma counting. To estimate the Bmax, Kd and Ki, the results of binding experiments are analyzed using SigmaPlot software (Jandel).

The binding affinities for the compounds of Formula I towards the $NPY_1$ receptor are expressed as $IC_{50}$ values and are less than 10 micromolar.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

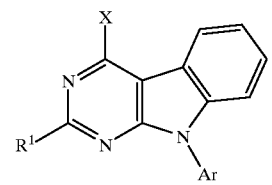

or the pharmaceutically acceptable salts thereof wherein
Ar is phenyl, 1- or 2-naphthyl, 2-, 3-, or 4-pyridyl, 2-, 4- or 5-pyrimidinyl, optionally mono-, di-, or tri-substituted with halogen, trifluoromethyl, hydroxy, amino, lower alkylamino, lower dialkylamino, carboxamido, N-lower alkyl carboxamido, N,N-lower dialkyl carboxamido, $C_1$–$C_6$ alkyl, $C_1$–$C_6$ alkoxy, with the proviso that at least one of the positions ortho or para to the point of attachment of Ar to the tricyclic ring system is substituted;

$R^1$ is hydrogen, halogen, trifluoromethyl, $C_1$–$C_6$ alkyl, or ($C_1$–$C_6$ alkyl)-$G^1$—$R^2$ where $G^1$ is oxygen or sulfur and $R^2$ is hydrogen or $C_1$–$C_6$ alkyl; and X is

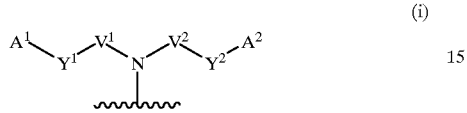

(i)

wherein
$V^1$ and $V^2$ are $CH_2$, CO, CS, $SO_2$ or $CH(C_1$–$C_6$ alkyl), with the proviso that both $V^1$ and $V^2$ cannot both be CO, CS or $SO_2$;

$Y^1$ and $Y^2$ independently represent a bond or $C_1$–$C_6$ alkylene;

$A^1$ is $NR^4R^5$ wherein $R^4$ and $R^5$ are independently hydrogen or a lower alkyl group, or $A^1$ is $NR^4R^5$ wherein $R^4$ is hydrogen or a $C_1$–$C_6$ alkyl group and $R^5$ forms a heterocyloalkyl group with $Y^1$ when $Y^1$ is alkylene; or $A^1$ is $C_1$–$C_6$ arylalkyl or $C_1$–$C_6$ heteroarylalkyl, where aryl is phenyl, and heteroaryl is 2-, 3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring; or $A^1$ is lower alkanoyl, lower alkylsulfonyl, with the proviso that $R^4$ and $R^5$ cannot both be alkanoyl or alkylsulfonyl; or $A^1$ is $NR^4R^5$ taken together form a $C_3$–$C_6$ heterocycloalkyl or a group of the formula:

wherein e and f are independently 1, 2 or 3 and the sum of e and f is at least 3; and
$G^2$ is
$NR^6$ wherein $R^6$ is hydrogen or $C_1$–$C_6$ alkyl, or $CH(C_0$–$C_6$ alkylene)-$G^3$—$R^7$ wherein $G^3$ is CONH, $CONH(C_1$–$C_6$ alkyl), NH, or $NH(C_1$–$C_6$ alkyl), and $R^7$ is hydrogen or $C_1$–$C_6$ alkyl; or
$CONH_2$, $CO[N(C_1$–$C_6$ alkyl)$R^8$] wherein $R^8$ is hydrogen or $C_1$–$C_6$ alkyl;
$C_1$–$C_6$ arylalkyl or $C_1$–$C_6$ heteroarylalkyl, where aryl is phenyl, and heteroaryl is 2-, 3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;

$A^2$ is hydrogen, $C_1$–$C_6$ alkyl, ($C_1$–$C_6$ alkylene)-$G^4$—$R^9$ wherein
$G^4$ is oxygen or sulfur and $R^9$ is hydrogen, trifluoromethyl or $C_1$–$C_6$ alkyl;

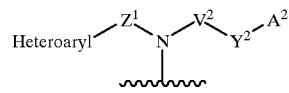

(ii)

wherein heteroaryl is 2-, 3- or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono- or disubstituted with halogen, trifluoromethyl, amino, $C_1$–$C_6$ alkyl, $C_1$–$C_6$ alkoxy, with the proviso that tetrazolyl can have at most one substituent;
$Z^1$ is $C_1$–$C_6$ alkyl; and
$V^2$, $Y^2$ and $A^2$ are as defined above;

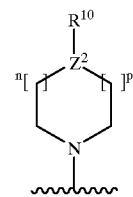

(iii)

where
$Z^2$ is CH, or nitrogen;
where
when $Z^2$ is CH, n is 0, 1, 2 or 3 and p is 1, 2, or 3, $R^{10}$ is carboxamido, or ($C_0$–$C_6$ alkylene)-$G^5$—$R^{11}$ wherein $G^5$ is NH, $NH(C_1$–$C_6$ alkyl) and $R^{11}$ is hydrogen, $C_1$–$C_6$ alkyl, $C_1$–$C_6$ arylalkyl or $C_1$–$C_6$ heteroarylalkyl, where aryl is phenyl, and heteroaryl is 2-, 3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring;
when $Z^2$ is carbon, n is 1 or 2 and p is 1 or 2, $R^{10}$ is amino; or
when $Z^2$ is nitrogen, n is 1 or 2 and p is 1 or 2, $R^{10}$ is hydrogen; or (iv) a nitrogen heterocycle of the formula:

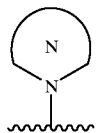

wherein the N-ring represents triazolyl, tetrazolyl, imidazolyl, or pyrazolyl, each of which is optionally substituted with amino, trifluoromethyl, carboxamido, or $(C_1-C_6$ alkylene)-$G^6$—$R^{12}$ wherein $G^6$ is NH, NH($C_1-C_6$ alkyl) and $R^{12}$ is hydrogen, $C_1-C_6$ alkyl, $C_1-C_6$ arylalkyl or $C_1-C_6$ heteroarylalkyl, where aryl is phenyl, and heteroaryl is 2-, 3-, or 4-pyridyl, 2-, 4- or 5-pyrimidinyl, 1-, 2- or 4-imidazolyl, 2-, 4-, or 5-oxazolyl, 2-, 4-, or 5-thiazolyl, 1-, 3- or 4-pyrazolyl, 1-, 3- or 4-triazolyl, 2-pyrazinyl, or 1-, 2- or 5-tetrazolyl, each of which is optionally mono-, di-, or tri-substituted with halogen, trifluoromethyl, hydroxy, amino, lower alkylamino, lower dialkylamino, lower alkylcarboxamido, lower alkyl, lower alkoxy, with the proviso that 2 adjacent substituents can together form a 5–7 fused cycloalkyl or heterocycloalkyl ring.

2. A compound according to claim 1, where W is CH, Ar is 2,4,6-trimethylphenyl, $R_1$ is methyl, and X is N-(2-aminoethyl)-N-(cyclopropylmethyl), N-(2-pyrrolidinoethyl)-N-(cyclopropylmethyl), N-(2-N',N'-dimethylaminoethyl)-N-(propyl), N-(2-(N',N'-dimethyl)aminoethyl)-N-(2-methoxyethyl), N-(2-(N',N'-dimethyl)aminoethyl)-N-(cyclopropylmethyl), N-(2-(N'-ethyl)aminoethyl)-N-(cyclopropylmethyl), N-(2-(N'-methyl-N'-ethyl)aminoethyl)-N-(cyclopropylmethyl), N-(2-(N',N'-diethyl)aminoethyl)-N-(cyclopropylmethyl), N-(2-(N'-methyl)aminoethyl)-N-(cyclopropylmethyl), N-(2-piperidinoethyl)-N-(cyclopropylmethyl), N-(2-pyrrolidinoethyl)-N-(propyl), N-(2-piperidinoethyl)-N-(propyl), N-(2-morpholinoethyl)-N-(cyclopropylmethyl), N-(2-(N'-methyl-N'-ethyl)aminoethyl)-N-(propyl), N-(2-(N'-methyl)piperazinyl)-N-(cyclopropylmethyl), N-(2-(N'-methyl)homopiperazinyl)-N-(cyclopropylmethyl), N-(2-(N'-isopropyl)aminoethyl)-N-(cyclopropylmethyl), N-(3-aminopropyl)-N-(cyclopropylmethyl), N-(2-aminoethyl)-N-(propyl), N-(2-aminoethyl)-N-(ethyl), N-(3-pyrrolidinopropyl)-N-(cyclopropylmethyl), N-(4-pyrrolidinobutyl)-N-(cyclopropylmethyl), N-(2-(N'-2-phenethyl)aminoethyl)-N-(cyclopropylmethyl), N-(2-pyrrolidinoethyl)-N-(2-methoxyethyl), N-(2-pyrrolidinoethyl)-N-(ethyl), N-(2-pyrrolidinoethyl)-N-(butyl), N-(2-pyrrolidinoethyl)-N-(isopropyl), N-(2-(N',N'-dimethyl)aminoethyl)-N-(isobutyl), N-(2-(N'-methyl-N'-ethyl)aminoethyl)-N-(isobutyl), N-(2-(N'-methylpyrrolidin-2-yl)ethyl)-N-(cyclopropylmethyl), N-(2-pyrrolidinoethyl)-N-(isopropyl), N-(2-(N',N'-dimethyl)aminoethyl)-N-(isopropyl), N-(2-(N'-cyclopentyl)aminoethyl)-N-(ethyl), N-(2-(N'-2-(4-methoxy)phenethyl)aminoethyl)-N-(ethyl), N-((1-methyl-2-pyrrolidino)ethyl)-N-(cyclopropylmethyl), N-((1-methyl-2-amino)ethyl)-N-(cyclopropyl methyl).

3. A compound according to claim 1, where W is CH, Ar is 2,4,6-trimethylphenyl, $R_1$ is methyl, and X is N-(1-oxo-2-(N',N'-dimethyl)aminoethyl)-N-(propyl), N-(2-oxo-2-(N',N'-dimethyl)aminoethyl)-N-(propyl), N-(1-oxo-2-(N',N'-dimethyl)aminoethyl)-N-(cyclopropylmethyl), N-(2-pyrrolidinoethyl)-N-(1-oxo-propyl), N-(2-pyrrolidinoethyl)-N-(1-oxo-cyclopropyl), N-(2-oxo-2-(N',N'-dimethyl)aminoethyl)-N-(cyclopropyl).

4. A compound according to claim 1, where W is CH, Ar is 2,4,6-trimethylphenyl, $R_1$ is methyl, and X is 2-(S)-(cyclopentylaminomethyl)pyrrolidinyl, 4-(carboxamido)piperidinyl, 3-(cyclopentylamino)pyrrolidinyl, 3-(1-oxo-2-((3-methoxy-4-ethoxy)phenyl)aminoethyl)pyrrolidinyl, 2-(2-(4-methoxy)phenyl)aminoethyl)pyrrolidinyl, 3-(1-oxo-2-((3-methoxy-4-ethoxy)phenyl)ethyl)pyrrolidinyl, 4-(2-((3-methoxy-4-ethoxy)phenyl)aminoethyl)piperidinyl.

5. A compound according to claim 1, where W is N, Ar is 2,4,6-trimethylphenyl, $R_1$ is methyl, and X is N-(2-pyrrolidinoethyl)-N-(cyclopropylmethyl), N-(2-pyrrolidinoethyl)-N-(propyl), N-(2-pyrrolidinoethyl)-N-(butyl), N-(2-pyrrolidinoethyl)-N-(cyclopropyl), N-(2-(N',N'-dimethyl)aminoethyl)-N-(propyl), N-(2-N',N'-dimethylaminoethyl)-N-(butyl), N-(2-(N',N'-dimethyl)aminoethyl)-N-(cyclopropylmethyl), N-(2-(N',N'-dimethyl)aminoethyl)-N-(cyclopropyl), N-(2-piperidinoethyl)-N-(propyl), N-(2-piperidinoethyl)-N-(butyl), N-(2-(N',N'-dimethyl)aminoethyl)-N-(cyclobutyl), N-(2-(N',N'-dimethyl)aminoethyl)-N-(cyclopentyl), N-(2-(N',N'-dimethyl)aminoethyl)-N-(2-methoxyethyl), N-(2-(N',N'-dimethyl)aminoethyl)-N-(isopropyl), N-(2-(N'-ethyl)aminoethyl)-N-(cyclopropyl), or piperazinyl.

6. A compound according to claim 1, where Ar is 2,6-dimethyl-4-bromophenyl, $R_1$ is methyl, and X is N-(2-(N',N'-dimethyl)aminoethyl)-N-(ethyl) or N-(2-pyrrolidinoethyl)-N-(cyclopropylmethyl).

7. A compound according to claim 1, where Ar is 2-methyl-4-methoxy phenyl, $R_1$ is methyl, and X is N-(2-(N',N'-dimethyl)aminoethyl)-N-(cyclopropylmethyl).

8. A compound according to claim 1, where Ar is 2,4-dimethylphenyl, $R_1$ is methyl, and X is N-(2-pyrrolidinoethyl)-N-(cyclopropylmethyl).

9. A compound according to claim 1, where W is CH, Ar is 2,6-dimethylphenyl, $R_1$ is methyl, and X is N-(2-(N',N'-dimethyl)aminoethyl)-N-(cyclopropylmethyl).

10. A compound according to claim 1, where W is CH, Ar is 2,4,6-trimethylphenyl, $R_1$ is methyl, and X is N-(2-(1-imidazolyl)aminoethyl)-N-(cyclopropylmethyl), N-(2-(1,2,4-triazol-4-yl)aminoethyl)-N-(cyclopropylmethyl).

11. A compound of the formula:

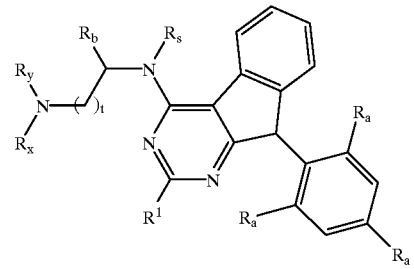

wherein each $R_a$ is independently $C_1$–$C_6$ alkyl;

$R_b$ is hydrogen or methyl;

$R_1$ is $C_1$–$C_6$ alkyl;

$R_s$ is $C_1$–$C_6$ alkyl, $(C_3$–$C_5)$cycloalkyl$(C_1$–$C_3)$alkyl, $(C_1$–$C_3)$alkoxy$(C_1$–$C_3)$alkyl, or $(C_3$–$C_5)$cycloalkyl;

t is 1, 2 or 3; and $R_x$ is hydrogen, $C_1$–$C_6$ alkyl, phenyl$(C_1$–$C_6)$alkyl where phenyl is optionally mono- or disubstituted independently with $C_1$–$C_6$ alkyl, $C_1$–$C_6$ alkoxy, halogen, or hydroxy; and $R_y$ is hydrogen, $C_1$–$C_6$ alkyl, $(C_3$–$C_6)$cycloalkyl; or $NR_xR_y$ represents pyrrolidinyl, N-($C_1$–$C_6$)alkylpyrrolidin-2-yl, piperidinyl, morpholinyl, or N-($C_1$–$C_6$)alkylpiperazinyl.

12. A compound according to claim 11, wherein $R_s$ is $C_1$–$C_6$ alkyl or cyclopropylmethyl.

13. A compound according to claim 12, wherein $R_s$ is cyclopropyl($C_1$–$C_3$)alkyl.

14. A compound according to claim 13, wherein $R_x$ and $R_y$ independently represent hydrogen or $C_1$–$C_2$ alkyl.

15. A compound according to claim 14, wherein each $R_a$ is methyl.

16. A compound of the formula:

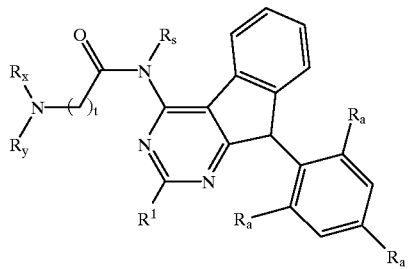

wherein
each $R_a$ is independently $C_1$–$C_6$ alkyl;
$R_1$ is $C_1$–$C_6$ alkyl;
$R_s$ is $C_1$–$C_6$ alkyl, cyclopropyl($C_1$–$C_3$)alkyl or ($C_1$–$C_3$)alkoxy($C_1$–$C_3$)alkyl;
t is 1 or 2;
$R_x$ is hydrogen, $C_1$–$C_6$ alkyl, phenyl($C_1$–$C_6$)alkyl where phenyl is optionally mono- or disubstituted independently with $C_1$–$C_6$ alkyl, $C_1$–$C_6$ alkoxy, halogen, or hydroxy; and
$R_y$ is hydrogen, $C_1$–$C_6$ alkyl, $(C_3$–$C_6)$cycloalkyl; or
$NR_xR_y$ represents pyrrolidinyl, N-($C_1$–$C_6$)alkylpyrrolidin-2-yl, piperidinyl, morpholinyl, or N-($C_1$–$C_6$)alkylpiperazinyl.

17. A compound according to claim 16, wherein $R_s$ is $C_1$–$C_6$ alkyl or cyclopropylmethyl.

18. A compound according to claim 17, wherein $R_s$ is cyclopropyl($C_1$–$C_3$)alkyl.

19. A compound according to claim 18, wherein t is 1 and $R_x$ and $R_y$ independently represent hydrogen or $C_1$–$C_2$ alkyl.

20. A compound according to claim 19, wherein each $R_a$ is methyl.

21. A compound of the formula:

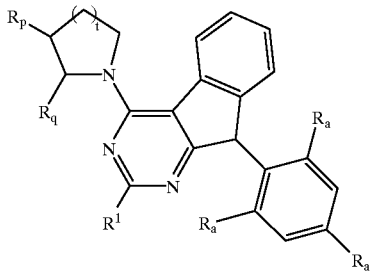

wherein
each $R_a$ is independently $C_1$–$C_6$ alkyl;
$R_1$ is $C_1$–$C_6$ alkyl;
t is 1 or 2;

$R_x$ and $R_y$ are different and represent hydrogen; ($C_3$–$C_7$)cycloalkylamino($C_1$–$C_3$)alkyl, carboxamido, ($C_3$–$C_7$)cycloalkylamino, $C_2$–$C_6$ alkanoyl optionally substituted in the ω-position with $C_1$–$C_6$ alkyl or phenyl optionally mono- or disubstituted independently with $C_1$–$C_6$ alkyl, $C_1$–$C_6$ alkoxy, halogen, or hydroxy, provided that at least one of $R_x$ and $R_y$ is hydrogen.

22. A compound according to claim 21, wherein $R^1$ is $C_1$–$C_2$ alkyl and W is nitrogen.

23. A compound according to claim 22, wherein each $R_a$ is methyl.

24. A compound according to claim 1 which is 4-(N-(2-Guanidinoethyl)-N-cyclopropylmethyl)amino-2-methyl-9-(2,4,6-trimethylphenyl)-9H-pyrimidino[4,5-b]indole.

25. A compound according to claim 1 which is 4-(N-(2-N',N'-Dimethylaminooethyl)-N-cyclopropyl)amino-2-methyl-9-(2,4,6-trimethylphenyl)-9H-pyrimidino[4,5-b]indole.

26. A compound according to claim 1 which is 4-(N-(2-N',N'-Dimethylaminoethyl)-N-methyl)amino-2-methyl-9-(2,4,6-trimethylphenyl)-9H-pyrimidino[4,5-b]indole;

4-(N-(2-N',N'-Dimethylaminoethyl)-N-ethyl)amino-2-methyl-9-(4-bromo-2,6-dimethylphenyl)-9H-pyrimidino[4,5-b]indole;

4-(N-(2-N',N'-Dimethylaminoethyl)-N-ethyl)amino-2-methyl-9-(4-clhoro-2-methylphenyl)-9H-pyrimidino[4,5-b]indole;

4-(N-(2-Morpholinoethyl)-N-propyl)amino-2-methyl-9-(2-chloro-4-methylphenyl)-9H-pyrimidino[4,5-b]indole;

4-(N-(2-N',N'-Dimethylaminoethyl)-N-cyclopropylmethyl)amino-2-methyl-9-(2,4,6-trimethylphenyl)-9H-pyrimidino[4,5-b]indole;

4-Piperazinyl-2-methyl-9-(2,4,6-trimethylphenyl)-9H-pyrimidino[4,5-b]indole;

4-(N-(2-Pyrrolidinoethyl)-N-cyclopropylmethyl)amino-2-methyl-9-(2,4,6-trimethylphenyl)-9H-pyrimidino[4,5-b]indole;

4-(3-Aminopyrrolidinyl)-2-methyl-9-(2,4,6-trimethylphenyl)-9H-pyrimidino[4,5-b]indole;

4-(2-(S)-Aminomethylpyrrolidino)-2-methyl-9-(2,4,6-trimethylphenyl)-9H-pyrimidino[4,5-b]indole; or 4-(3-Amino-2-triazolyl)-2-methyl-9-(2,4,6-trimethylphenyl)-9H-pyrimidino[4,5-b]indole.

27. A compound according to claim 1 which is 4-(3-Amino-1-triazolyl)-2-methyl-9-(2,4,6-trimethylphenyl)-9H-pyrimidino[4,5-b]indole;

4-(3-Amino-4-triazolyl)-2-methyl-9-(2,4,6-trimethylphenyl)-9H-pyrimidino[4,5-b]indole;

4-(N-(2-Pyrrolidinoethyl)-N-cyclopropylmethyl)amino-2-methyl-9-(4-bromo-2,6-dimethylphenyl)-9H-pyrimidino[4,5-b]indole;

4-(N-(2-Pyrrolidinoethyl)-N-propyl)amino-2-methyl-9-(2,4,6-trimethylphenyl)-9H-pyrimidino[4,5-b]indole;

4-(N-(2-Pyrrolidinoethyl)-N-butyl)amino-2-methyl-9-(2,4,6-trimethylphenyl)-9H-pyrimidino[4,5-b]indole;

4-(N-(2-Pyrrolidinoethyl)-N-cyclopropyl)amino-2-methyl-9-(2,4,6-trimethylphenyl)-9H-pyrimidino[4,5-b]indole;

4-(N-(2-N',N'-Dimethylaminooethyl)-N-propyl)amino-2-methyl-9-(2,4,6-trimethylphenyl)-9H-pyrimidino[4,5-b]indole;

4-(N-(2-N',N'-Dimethylaminoethyl)-N-butyl)amino-2-methyl-9-(2,4,6-trimethylphenyl)-9H-pyrimidino[4,5-b]indole;

4-(N-(2-Piperidinoethyl)-N-propyl)amino-2-methyl-9-(2,4,6-trimethylphenyl)-9H-pyrimidino[4,5-b]indole; or 4-(N-(2-Piperidinoethyl)-N-butyl)amino-2-methyl-9-(2,4,6-trimethylphenyl)-9H-pyrimidino[4,5-b]indole.

28. A compound according to claim 1 which is 4-(N-(2-N',N'-Dimethylaminoethyl)-N-cyclobutyl)amino-2-methyl-9-(2,4,6-trimethylphenyl)-9H-pyrimidino[4,5-b]indole;

4-(N-(2-N',N'-Dimethylaminoethyl)-N-cyclopentyl)amino-2-methyl-9-(2,4,6-trimethylphenyl)-9H-pyrimidino[4,5-b]indole;

4-(N-(2-N',N'-Dimethylaminoethyl)-N-isopropyl)amino-2-methyl-9-(2,4,6-trimethylphenyl)-9H-pyrimidino[4,5-b]indole;

4-(N-(2-N'-Methylaminoethyl)-N-methyl)amino-2-methyl-9-(2,4,6-trimethylphenyl)-9H-pyrimidino[4,5-b]indole;

4-(4-(N-Methylamino)piperidino)-2-methyl-9-(2,4,6-trimethylphenyl)-9H-pyrimidino[4,5-b]indole;

4-(4-(2-Aminoethyl)piperazinyl)-2-methyl-9-(2,4,6-trimethylphenyl)-9H-pyrimidino[4,5-b]indole;

4-(N-(2-N'-Ethylaminoethyl)-N-ethyl)amino-2-methyl-9-(2,4,6-trimethylphenyl)-9H-pyrimidino[4,5-b]indole;

(±)-4-(N-(2-N',N'-Dimethylaminoethyl)-N-1-methylpropyl)amino-2-methyl-9-(2,4,6-trimethylphenyl)-9H-pyrimidino[4,5-b]indole;

4-(N-(2-N',N'-Diethylaminoethyl)-N-cyclopropylmethyl)amino-2-methyl-9-(2,4,6-trimethylphenyl)-9H-pyrimidino[4,5-b]indole; or 4-(N-(2-N',N'-Diethylaminoethyl)-N-cyclopropyl)amino-2-methyl-9-(2,4,6-trimethylphenyl)-9H-pyrimidino[4,5-b]indole.

29. A compound according to claim 1 which is 4-(N-(2-N',N'-Dimethylaminoethyl)-N-2-methoxyethyl)amino-2-methyl-9-(2,4,6-trimethylphenyl)-9H-pyrimidino[4,5-b]indole;

4-(N-(2-N',N'-Dimethylaminoethyl)-N-2-ethoxyethyl)amino-2-methyl-9-(2,4,6-trimethylphenyl)-9H-pyrimidino[4,5-b]indole;

4-(N-(2-N'-Ethylaminoethyl)-N-ethyl)amino-2-methyl-9-(2-methyl-4-chlorophenyl)-9H-pyrimidino[4,5-b]indole;

4-(N-(Cyclopentylaminopiperidin-4-yl)-N-ethyl)amino-2-methyl-9-(2,4,6-trimethylphenyl)-9H-pyrimidino[4,5-b]indole;

4-(N-(2-N',N'-Dimethylaminoethyl)-N-isobutyl)amino-2-methyl-9-(2,4,6-trimethylphenyl)-9H-pyrimidino[4,5-b]indole;

4-(N-(2-(3-Methoxy-4-ethoxy)phenethyl)aminopiperidin-4-yl)-N-ethyl)amino-2-methyl-9-(2,4,6-trimethylphenyl)-9H-pyrimidino[4,5-b]indole;

4-(N-(S)-(1-Oxo-2-(4-methoxy)phenethyl)aminopyrrolidin-2-yl)-2-methyl-9-(2,4,6-trimethylphenyl)-9H-pyrimidino[4,5-b]indole; or 4-(N-(S)-(2-(4-Methoxy)phenethyl)aminopyrrolidin-2-yl)-2-methyl-9-(2,4,6-trimethylphenyl)-9H-pyrimidino[4,5-b]indole.

30. A method of treating anxiety, depression, post-traumatic stress disorder, inflammatory diseases, or obesity, in mammals, comprising administering to the mammal a therapeutically effective amount of a compound of claim 1.

31. A pharmaceutical composition comprising a compound according to claim 1 together with at least one pharmaceutically acceptable carrier or excipient.

\* \* \* \* \*